(12) United States Patent
Honebrink et al.

(10) Patent No.: US 7,553,305 B2
(45) Date of Patent: Jun. 30, 2009

(54) PUSH-PULL WIRE ANCHOR

(75) Inventors: Brian Honebrink, Stillwater, MN (US); Brian Fischer, Minneapolis, MN (US)

(73) Assignee: Enpath Medical, Inc., Minneapolis, MN (US)

( * ) Notice: Subject to any disclaimer, the term of this patent is extended or adjusted under 35 U.S.C. 154(b) by 679 days.

(21) Appl. No.: 11/149,079

(22) Filed: Jun. 9, 2005

(65) Prior Publication Data
US 2007/0005008 A1 Jan. 4, 2007

(51) Int. Cl.
*A61M 25/00* (2006.01)
(52) U.S. Cl. .................. 604/528; 604/524; 604/264
(58) Field of Classification Search ............. 604/95.04, 604/264, 523–529; 607/126
See application file for complete search history.

(56) References Cited

U.S. PATENT DOCUMENTS

| | | | |
|---|---|---|---|
| 4,586,923 A | 5/1986 | Gould et al. | |
| 4,886,067 A | 12/1989 | Palermo | |
| 4,898,577 A | 2/1990 | Badger et al. | |
| 4,921,482 A | 5/1990 | Hammerslag et al. | |
| 4,964,409 A | 10/1990 | Tremulis | |
| 4,998,916 A | 3/1991 | Hammerslag et al. | |
| 5,108,368 A | 4/1992 | Hammerslag et al. | |
| 5,190,050 A | 3/1993 | Nitzsche | |
| 5,195,968 A | 3/1993 | Lundquist et al. | |
| 5,199,950 A | 4/1993 | Schmitt et al. | |
| 5,203,772 A | 4/1993 | Hammerslag et al. | |
| 5,254,088 A | 10/1993 | Lundquist et al. | |
| 5,299,580 A | 4/1994 | Atkinson et al. | |
| 5,308,324 A | 5/1994 | Hammerslag et al. | |
| RE34,695 E | 8/1994 | Mar et al. | |
| 5,336,182 A | 8/1994 | Lundquist et al. | |
| 5,345,937 A | 9/1994 | Middleman et al. | |
| 5,358,478 A | 10/1994 | Thompson et al. | |
| 5,358,479 A | 10/1994 | Wilson | |
| 5,368,564 A | 11/1994 | Savage | |
| 5,372,587 A | 12/1994 | Hammerslag et al. | |
| 5,391,146 A | 2/1995 | That et al. | |
| 5,395,327 A | 3/1995 | Lundquist et al. | |
| 5,399,164 A | 3/1995 | Snoke et al. | |
| 5,480,382 A | 1/1996 | Hammerslag et al. | |
| 5,531,686 A | 7/1996 | Lundquist et al. | |

(Continued)

FOREIGN PATENT DOCUMENTS

EP 0815895 A1 1/1998

(Continued)

OTHER PUBLICATIONS

"International Search Report for corresponding PCT Application No. PCT/US2006/022531", (Oct. 5, 2006), 5 pgs.

(Continued)

*Primary Examiner*—Rebecca E Eisenberg
(74) *Attorney, Agent, or Firm*—Schwegman, Lundberg & Woessner, P.A.

(57) ABSTRACT

A deflectable catheter includes a flexible element includes a flexible element, and at least one skirt extending at least part way around the flexible element. An encapsulant is coupled between the skirt and a deflectable distal end portion of the deflectable catheter. The encapsulant is adapted to transmit pushing and pulling forces from the skirt to the deflectable distal end portion.

28 Claims, 16 Drawing Sheets

U.S. PATENT DOCUMENTS

| | | | |
|---|---|---|---|
| 5,545,200 A | 8/1996 | West et al. | |
| 5,562,619 A | 10/1996 | Mirarchi et al. | |
| 5,579,779 A | 12/1996 | Humphrey | |
| 5,662,606 A | 9/1997 | Cimino et al. | |
| 5,676,653 A | 10/1997 | Taylor et al. | |
| 5,779,646 A | 7/1998 | Koblish et al. | |
| 5,830,155 A | 11/1998 | Frechette et al. | |
| 5,891,088 A | 4/1999 | Thompson et al. | |
| 5,893,885 A | 4/1999 | Webster, Jr. | |
| 5,897,529 A | 4/1999 | Ponzi | |
| 5,957,863 A | 9/1999 | Koblish et al. | |
| 6,004,291 A | 12/1999 | Ressemann et al. | |
| 6,064,905 A | 5/2000 | Webster, Jr. et al. | |
| 6,066,125 A | 5/2000 | Webster, Jr. | |
| 6,123,699 A | 9/2000 | Webster, Jr. | |
| 6,146,355 A | 11/2000 | Biggs | |
| 6,198,974 B1 | 3/2001 | Webster, Jr. | |
| 6,203,507 B1 | 3/2001 | Wadsworth et al. | |
| 6,251,092 B1 | 6/2001 | Qin et al. | |
| 6,355,016 B1 | 3/2002 | Bagaoisan et al. | |
| 6,375,629 B1 | 4/2002 | Muni et al. | |
| 6,398,776 B1 * | 6/2002 | Sekino et al. | 604/524 |
| 6,402,719 B1 | 6/2002 | Ponzi et al. | |
| 6,500,167 B1 | 12/2002 | Webster, Jr. | |
| 6,530,897 B2 | 3/2003 | Nardeo | |
| 6,544,215 B1 | 4/2003 | Bencini et al. | |
| 6,571,131 B1 | 5/2003 | Nguyen | |
| 6,582,536 B2 | 6/2003 | Shimada | |
| 6,602,242 B1 * | 8/2003 | Fung et al. | 604/528 |
| 6,607,496 B1 | 8/2003 | Poor et al. | |
| 6,616,628 B2 | 9/2003 | Hayzelden | |
| 6,669,670 B1 | 12/2003 | Muni et al. | |
| 6,706,010 B1 | 3/2004 | Miki et al. | |
| 6,783,521 B2 | 8/2004 | Ponzi et al. | |
| 6,976,979 B2 * | 12/2005 | Lawrence et al. | 604/524 |
| 2002/0165534 A1 | 11/2002 | Hayzelden et al. | |
| 2003/0109861 A1 | 6/2003 | Shimada | |
| 2003/0135156 A1 | 7/2003 | Bencini et al. | |
| 2003/0135199 A1 | 7/2003 | Rosenman et al. | |
| 2003/0181827 A1 | 9/2003 | Hojeibane et al. | |
| 2003/0187389 A1 | 10/2003 | Morency et al. | |
| 2003/0233058 A1 | 12/2003 | Ewers et al. | |
| 2003/0236492 A1 * | 12/2003 | Honebrink | 604/95.04 |
| 2003/0236493 A1 | 12/2003 | Mauch | |
| 2004/0097819 A1 | 5/2004 | Duarte | |
| 2004/0116848 A1 | 6/2004 | Gardeski et al. | |

FOREIGN PATENT DOCUMENTS

| | | |
|---|---|---|
| EP | 1038545 A2 | 9/2000 |
| EP | 1205208 A1 | 5/2002 |
| JP | 08-112245 | 5/1996 |
| WO | WO-01/78825 A2 | 10/2006 |
| WO | WO-2006/135774 A1 | 12/2006 |
| WO | WO-2006/135774 C2 | 2/2007 |

OTHER PUBLICATIONS

"European Application Serial No. 06772732.1, Office Action mailed Apr. 7, 2008"; 4 pages.

* cited by examiner

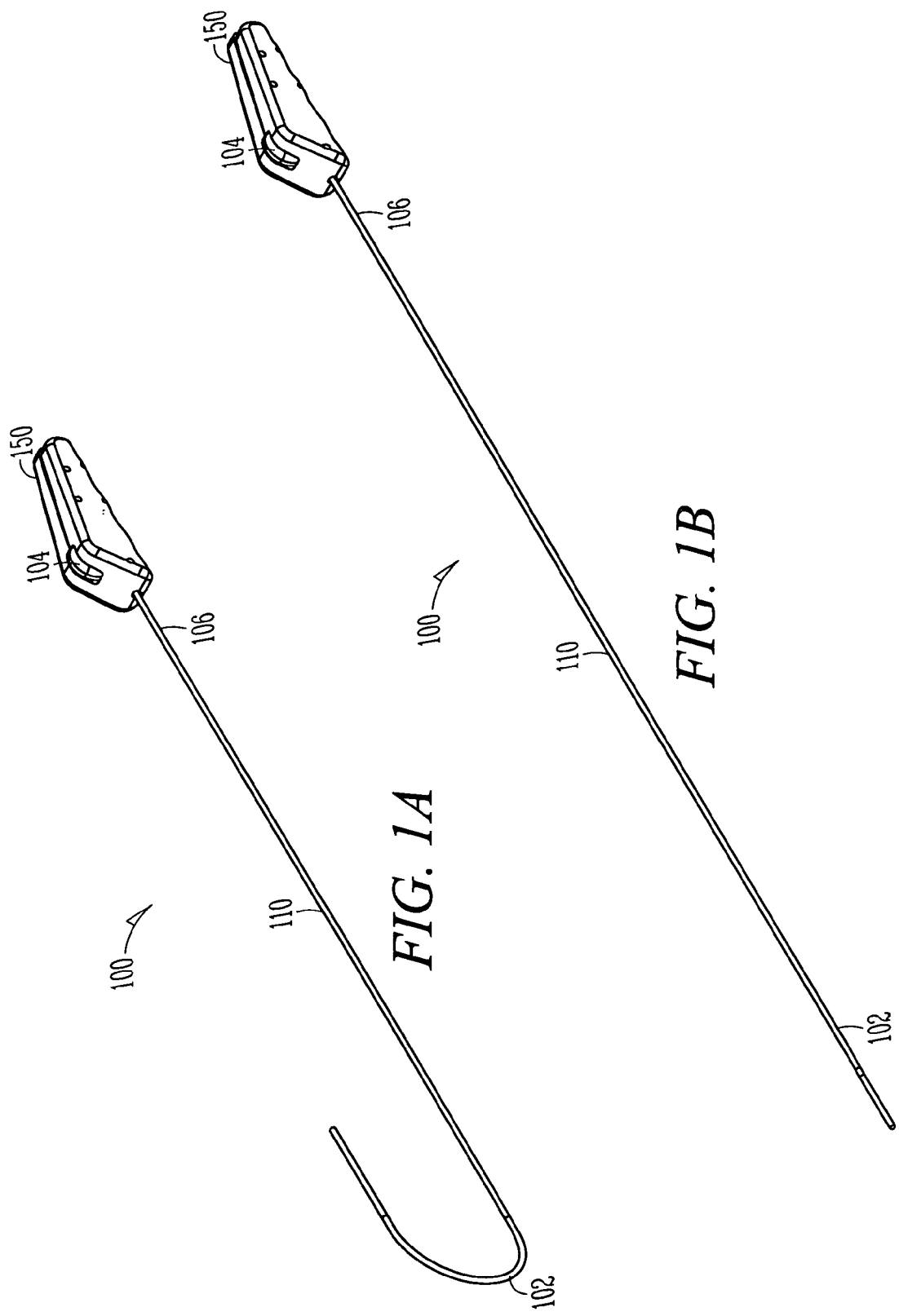

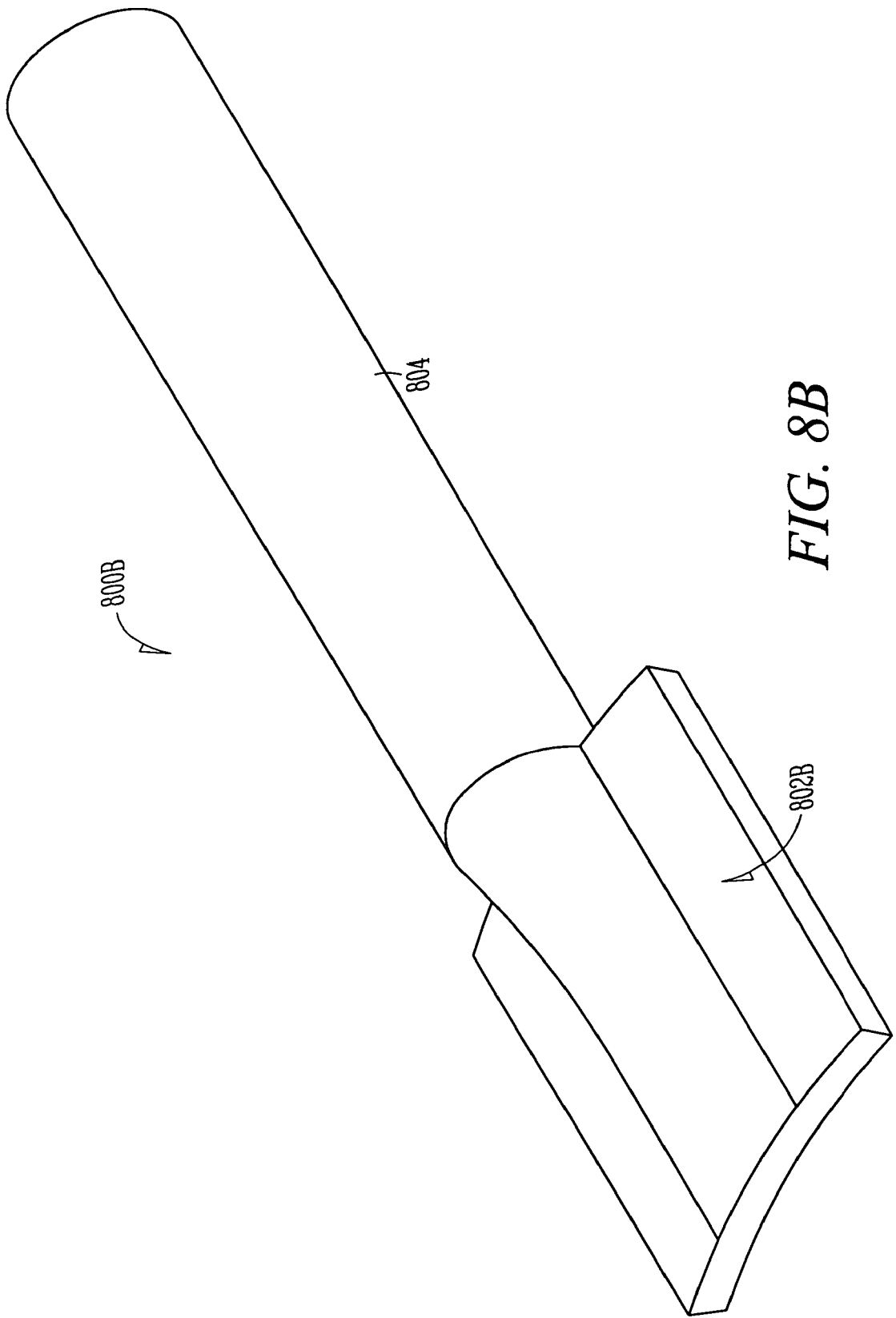

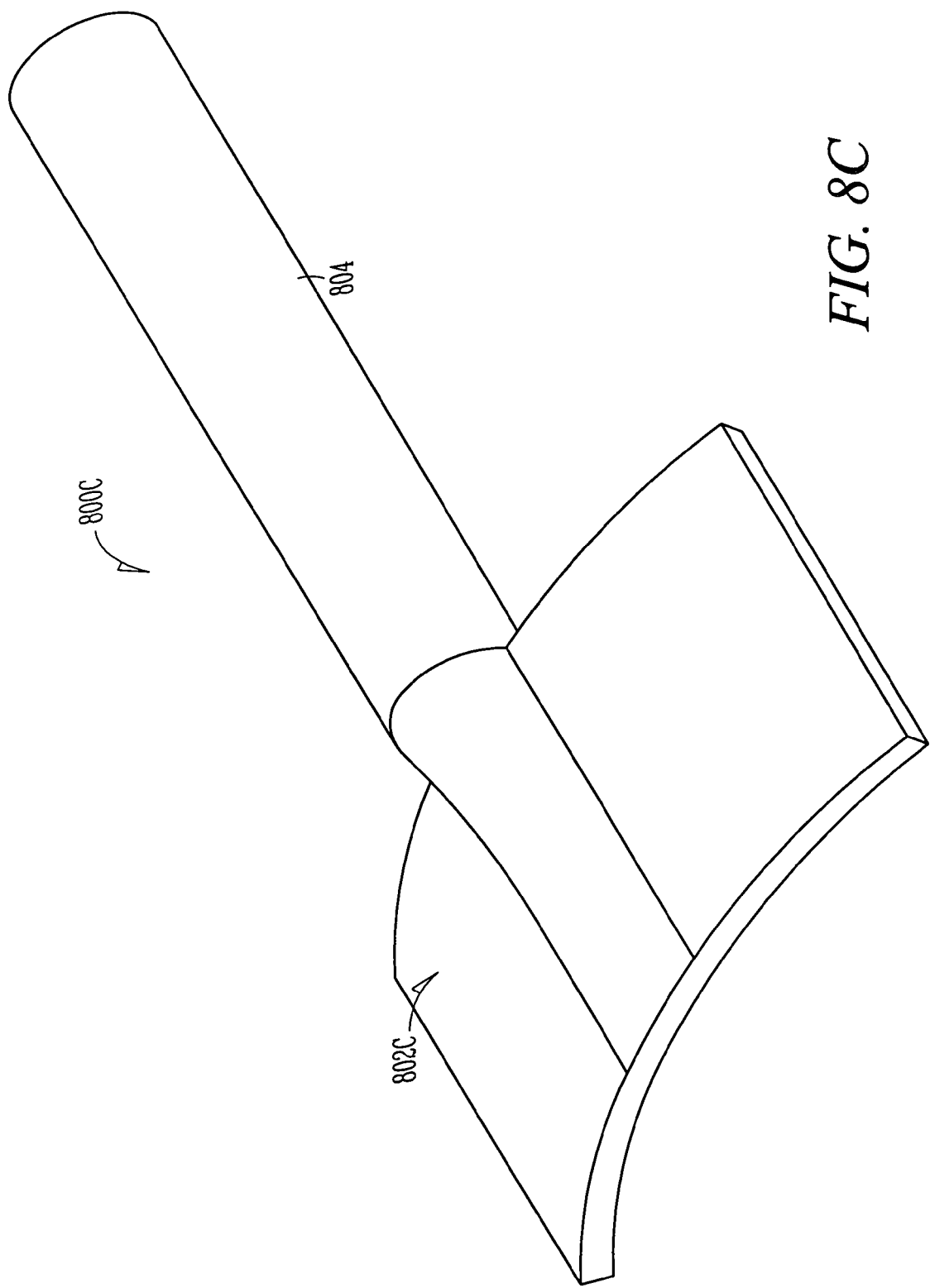

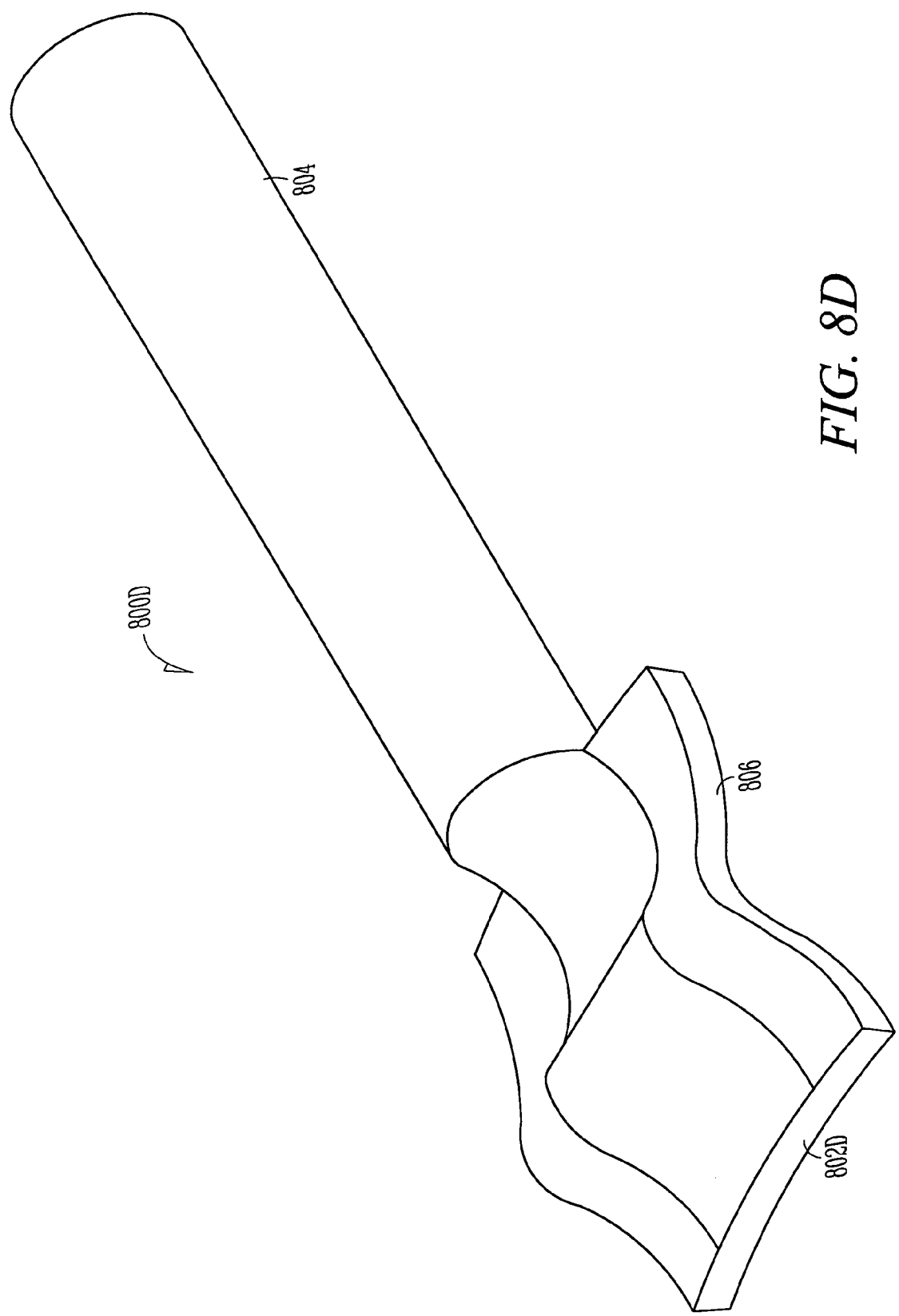

PUSH-PULL WIRE ANCHOR

TECHNICAL FIELD

A push-pull wire anchor and in particular a push-pull wire anchor in a deflectable catheter for transmitting pushing and pulling forces without failure of the catheter.

BACKGROUND

It is often difficult to provide reliable couplings between a push-pull wire and the deflectable distal end portion of a deflectable catheter. Welding or soldering the push-pull wire to a marker band in the deflectable distal end portion can anneal a portion of the wire adjacent to the weld. The annealed portion of the wire is sometimes weakened relative to the rest of the push-pull wire. When the push-pull wire experiences the stress of repeated pushing and pulling from an actuator the wire may fracture in the annealed region. Additionally, the marker band extends remotely from the push-pull wire around the catheter body. Pushing and pulling forces can tear the pull ring apart through shearing forces thereby freeing the push-pull wire to undesirably move within the catheter.

Often, the deflectable distal end portion of the catheter is in a deflected position within a curved vessel when the push-pull wire fractures. If pushing forces are applied to the push-pull wire after fracture, the fractured end of the push-pull wire may puncture the sidewall of the deflected catheter. Further, if the catheter is in a substantially non-deflected position and pushing forces are applied to deflect the catheter, the fractured end of the push-pull wire may puncture the distal end of the catheter.

Moreover, fracturing the wire prevents transmission of pushing and pulling forces to the deflectable distal end portion. Failure of the push-pull wire can complicate a medical procedure. For instance, the catheter must be withdrawn through curving vasculature, possibly in a deflected position created prior to fracture of the push-pull wire. The deflected catheter can snag within the vasculature and complicate the extraction. Further, the catheter must be exchanged with another deflectable catheter and the vasculature traversed again to complete the medical procedure.

In other examples, the push-pull wire is retained within a deflectable distal end portion by adhesives and the like. Assembling a catheter with an adhered push-pull wire is complex and requires hollowing out a portion of the catheter and injecting the adhesive into the hollowed out portion of the catheter to couple the push-pull wire with the deflectable distal end portion. In still other examples, the push-pull wire is adhered to the catheter with a hardened distal end portion. The push-pull wire is potted (i.e., covered on its distal and side surfaces) with the adhesive that forms the distal end portion. Compressive stresses from the push-pull wire can dislodge the distal end portion and cause failure of the catheter. Additionally, the adhesives used to form the distal end portion create a hard structure that has little or no deformability and can therefore be traumatic when engaged against the soft tissues of vasculature and organs.

What is needed is a push-pull wire anchor that overcomes the shortcomings of previous designs. What is further needed is a push-pull wire anchor that substantially prevents fracture of the push-pull wire and puncturing of a catheter by a fractured push-pull wire.

SUMMARY

A deflectable catheter for a catheter assembly includes a catheter body including a deflectable distal end portion. A flexible element (e.g., a push-pull wire) including a flexible element distal portion extends along at least a portion of the deflectable distal end portion. At least one anchor, such as a skirt extends at least part way around the flexible element distal portion and is coupled with the flexible element. In one option, the skirt is integral to the flexible element distal portion. An encapsulant is coupled between the skirt and the deflectable distal end portion. The encapsulant is adapted to transmit pushing and pulling forces from the skirt to the deflectable distal end portion, and the encapsulant forms at least a portion of an outer surface of the deflectable distal end portion. The tension strength and compression strength of the flexible element and the at least one skirt are at least as strong as the encapsulant tension strength and compression strength. The skirt includes at least one recess (e.g., holes, corrugations, grooves or the like) dimensioned and configured to receive the encapsulant, in yet another option.

Several options for the deflectable catheter follow. In one option, at least one weld couples the flexible element distal portion to the deflectable distal end portion, and the at least one weld is distal to the at least one skirt. In another option, the at least one skirt includes a flared portion.

The flared portion includes at least one recess (e.g., hole, corrugation or the like) optionally.

The at least one skirt includes, in yet another option, a clamp substantially surrounding the flexible element distal portion. The clamp is crimped at a plurality of points along the clamp, optionally.

In another option, at least one of the skirt and the flexible element distal portion include at least one projection. At least one of the skirt and the distal portion include at least one recess sized and shaped to receive the at least one projection, optionally. In yet another option, the at least one projection extends from the skirt and engages against the flexible element distal portion substantially immobilizing the at least one skirt relative to the flexible element. In still another option, the skirt includes knurling, brazing dots or the like.

A method for making a deflectable catheter includes positioning a flexible element along a catheter liner. A distal portion of the flexible element extends along at least a portion of a deflectable distal end portion of the catheter liner. At least one skirt is coupled to the distal portion, and the at least one skirt extends at least part way around the flexible element distal portion. The method further includes positioning an encapsulant around at least the flexible element distal portion and the deflectable distal end portion. The encapsulant is squeezed around the flexible element distal portion and the skirt, and the encapsulant forms at least a portion of a sidewall of the deflectable distal end portion and at least the skirt is within the sidewall. The encapsulant is adapted to transmit pushing and pulling forces from the at least one skirt to the deflectable distal end portion. The tension strength and compression strength of the flexible element and the at least one skirt are at least as strong as the encapsulant tension strength and compression strength.

Several options for the method follow. In one option, the method includes substantially preventing a puncture of the encapsulant by the flexible element (e.g., the encapsulant grasps the skirt and the skirt is coupled to the flexible element). In another option, a marker band is coupled substantially adjacent to the deflectable distal end portion. The marker band is distal relative to the skirt. The flexible element distal portion is welded to the marker band. The method includes, in yet another option, substantially preventing fracture of the flexible element adjacent to the marker band.

In another option, the skirt includes a clamp, and the clamp is deformed to grasp the flexible element distal portion. The clamp is crimped at a plurality of points along the clamp, optionally. The method includes, in yet another option, engaging a projection extending from at least one of the skirt and the flexible element distal portion against the other of the skirt and the distal portion. In still another option, engaging the projection includes seating the projection within at least one recess sized and shaped to receive the projection, wherein the recess is formed in at least one of the skirt and the flexible element distal portion. Optionally, the method includes deforming at least one of the flexible element and the skirt with the projection to form the recess.

The above described catheter allows for deflection of a deflectable distal end portion while substantially preventing fracture of a flexible element. Pushing and pulling forces from the flexible element are transmitted through the skirt to the encapsulant and the catheter liner at the deflectable distal end portion of the catheter. The skirt anchored in the encapsulant facilitates deflection of the deflectable distal end portion through transmission of the pushing and pulling forces. In one option, the skirt is integral to the flexible element distal portion. Where the flexible element distal portion is not coupled to a marker band optionally, the skirt and the flexible element are disposed along the catheter body proximal to a marker band used to see the tip of the catheter body during procedures (e.g., with fluoroscopy). Proximally positioning the skirt provides additional space to include features, for instance flush openings and the like, positioned between the skirt and marker band.

The flexible element and the skirt have tension and compression strengths at least as great as the tension and compression strengths of the encapsulant to substantially reduce fracture of the flexible element. Optionally, the catheter body is adapted to fail before failure of the flexible element and the skirt, and puncturing of the catheter body is thereby substantially prevented by a fractured element. In another option, the skirt is coupled to the flexible element distal portion without a weld. Fracturing of the flexible element is thereby substantially reduced because stress is not applied to a weakened annealed region. Additionally, the skirt is localized around the flexible element without extending remotely around the deflectable distal end portion. The skirt thus provides improved strength and durability against failure through shearing. Moreover, because the skirt is localized substantially adjacent to the flexible element pushing and pulling forces are not distributed around the catheter body. The deflectable distal end portion thus experiences an improved deflection response with the concentrated pushing and pulling of the flexible element.

In another option, the skirt cooperates with the marker band coupled to the flexible element distal portion. The marker band is coupled to the flexible element distally relative to the skirt. The skirt acts as a supplementary anchor and distributes pushing and pulling forces between the marker band and itself. Fracturing of the flexible element adjacent to the marker band (e.g., the annealed region near a weld) is substantially reduced because the pushing and pulling forces are distributed between the skirt and the marker band. Additionally, where the flexible element distal portion does fracture adjacent the marker band, the skirt embedded in the encapsulant acts to substantially immobilize the fractured flexible element and substantially prevent puncturing of the catheter body. Moreover, the skirt facilitates continued use of the catheter with a fractured flexible element because the skirt continues to function as an anchor and transmits pushing and pulling forces to the deflectable distal end portion.

Additionally, the encapsulant is squeezed around the catheter liner to easily form an outer surface and sidewall of the catheter body and grasp the skirt. In one option, the skirt is in the sidewall and thereby provides a larger moment to the deflectable distal end portion because it is positioned remotely from the center of the catheter body. As described above, the encapsulant flows around the skirt and, when hardened, transmits tension and compression forces to the deflectable distal end portion while also acting as the outer surface of the catheter body. Complex manufacturing procedures including drilling and/or forming a pocket for an anchor and injecting an adhesive over the anchor are thereby avoided. Further, the skirt is retained along the catheter body and the distal end therefore does not house the skirt and/or the flexible element in a hard tip. In one option, the distal end of the catheter body thereby has a soft atraumatic tip.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 1A is a perspective view of one example of a catheter in a first deflected position.

FIG. 1B is a perspective view of the catheter in a non-deflected position.

FIG. 8B is a perspective view of one example of an anchor.

FIG. 8C is a perspective view of another example of an anchor.

FIG. 8D is a perspective view of yet another example of an anchor.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1C:
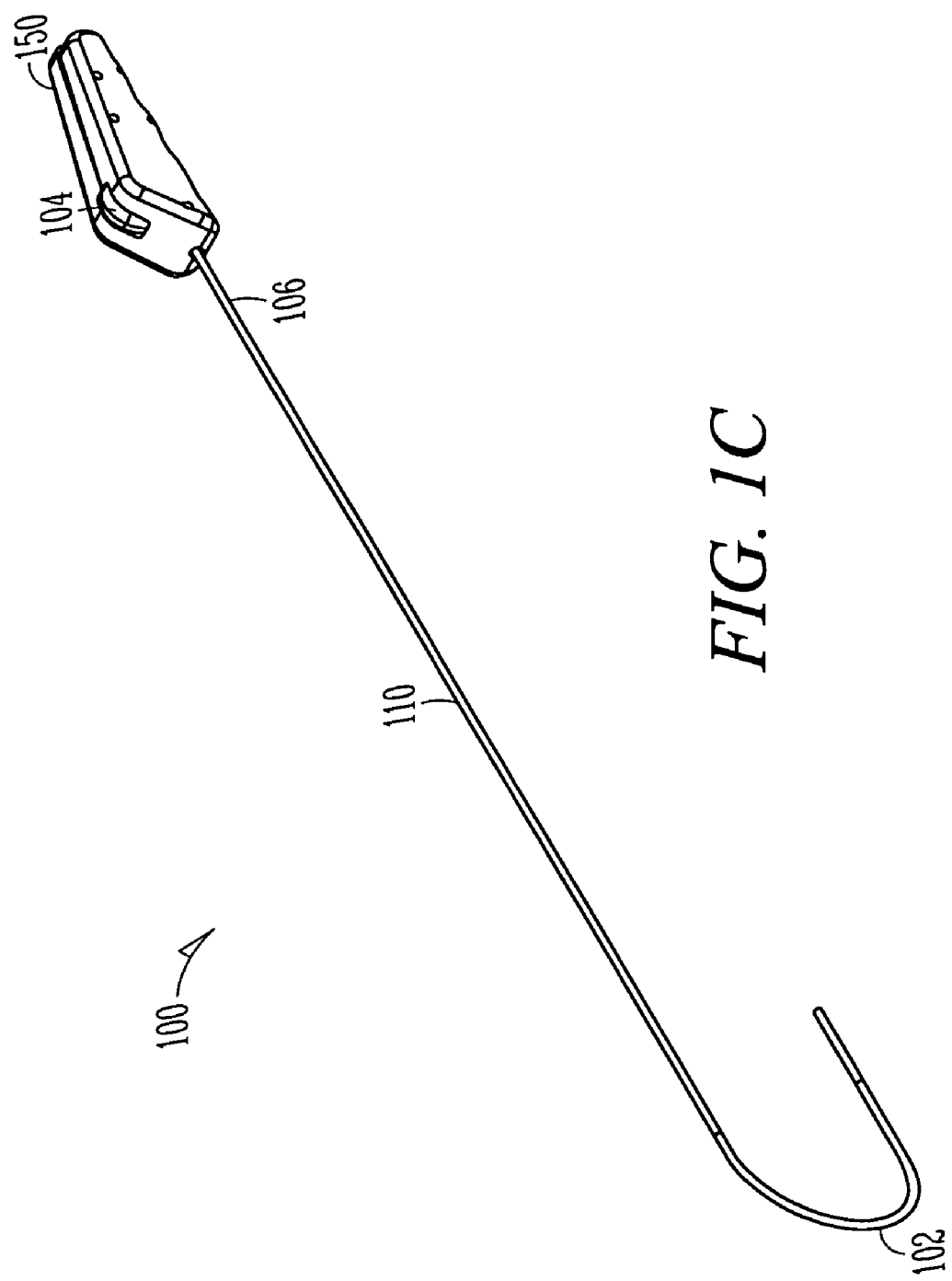
FIG. 1C is a perspective view of the catheter in a second deflected position.

FIGS. 1A, B, C illustrate a deflectable catheter assembly 100, where FIG. 1A illustrates the deflectable catheter assembly 100 in one articulated position, and FIG. 1C illustrates the catheter assembly in another articulated orientation. FIG. 1B illustrates the deflectable catheter assembly 100 in an unarticulated position. The deflectable catheter assembly 100 includes a catheter body 110 and a handle assembly 150 that houses actuating mechanisms for deflecting the catheter body 110. The handle assembly 150 allows for the selectable deflection of a deflectable distal end portion 102 of the catheter body 110 into any number of disparate orientations. One example of the handle assembly 150 is described in co-pending application Ser. No. 10/179,633, assigned to Enpath Medical, Inc., entitled ARTICULATING HANDLE FOR A DEFLECTABLE CATHETER, which is incorporated herein by reference. As shown in FIGS. 1A, B, C the actuating mechanism includes a wheel 104. The wheel 104 is rotated to deflect the deflectable distal end portion 102 into the orientations shown in FIGS. 1A, C. In another option, the handle assembly 150 includes a slide, knob, pull ring or the like to facilitate deflection of the deflectable distal end portion 102.

As shown in FIGS. 2-10, the catheter body 110 includes a flexible element 200, for instance a push-pull wire or the like. Optionally, the flexible element 200 is constructed with, but is not limited to steel, polymers or the like. The flexible element 200 is coupled between the actuating mechanisms in the handle assembly 150 (FIG. 1) and the deflectable distal end portion 102. As shown in FIGS. 1A, C, when tension or compression is applied to the flexible element 200 (e.g., using the wheel 104), corresponding pushing or pulling forces are experienced by the deflectable distal end portion 102 causing the deflectable distal end portion 102 to curve in predetermined directions. The distal end portion 102 is deflected, in one option, to traverse vasculature with the catheter assembly 100.

Referring again to FIGS. 1A, B, C, the catheter body 110 includes an elongate tubular construction that is flexible yet substantially non-compressible along its length. The deflectable catheter body 110 extends from a proximal end 106 to the deflectable distal end portion 102. The deflectable distal end portion 102, in one option, is adapted to be disposed within a patient. As described above, at the proximal end 106 the deflection of the deflectable catheter body 110 is controlled with the handle assembly 150 containing the actuator mechanism coupled to the flexible element 200 (FIG. 2) and the wheel 104. The distal end portion 102 is deflected to traverse various branch vessels with the catheter assembly 100 (FIGS. 1A and 1C).

Figure 2:
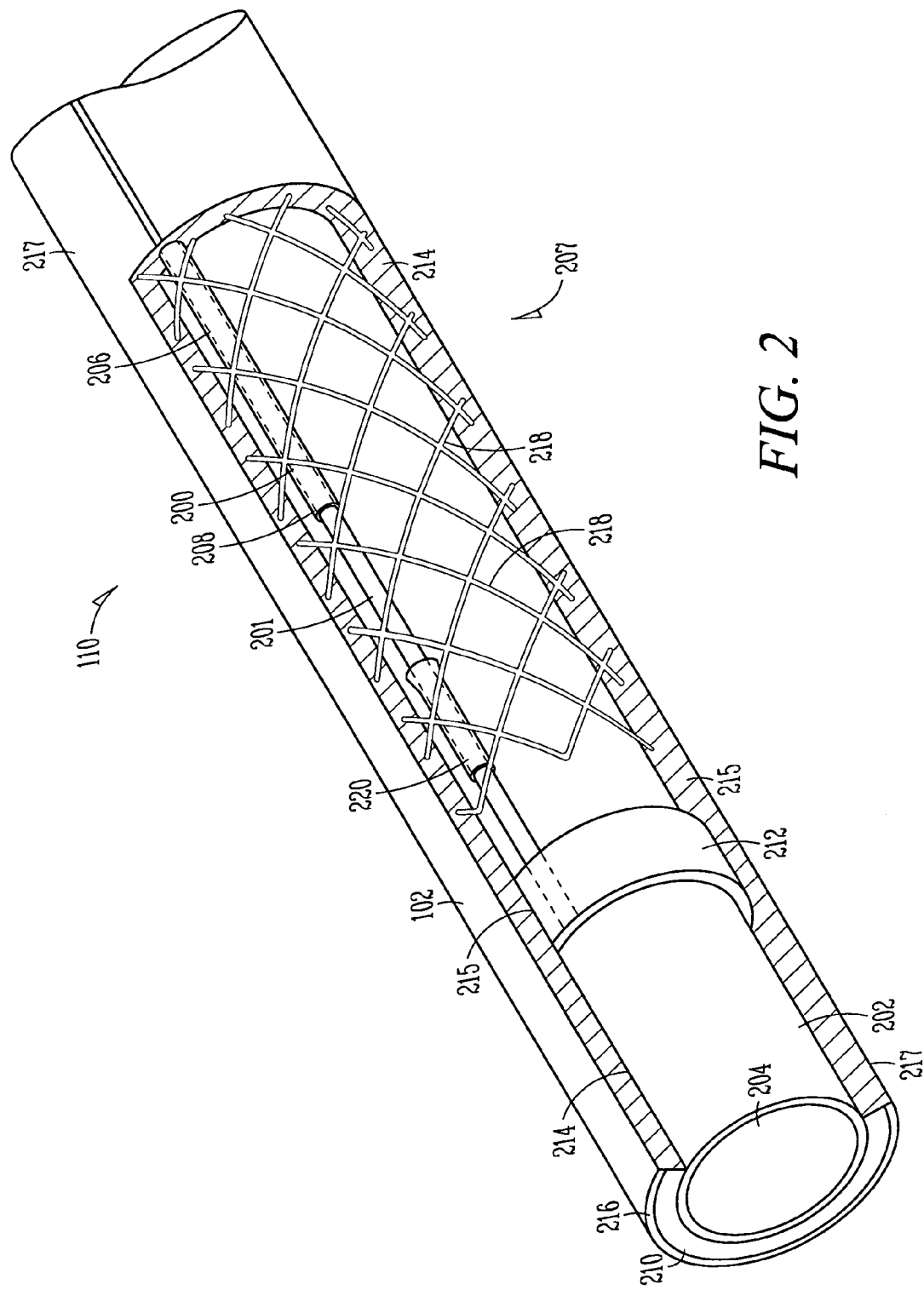
FIG. 2 is a perspective view of one example of the deflectable distal end portion.

FIG. 2 illustrates a partial cut-away of one example of the deflectable distal end portion 102 of the catheter body 110 shown in FIGS. 1A, B, C. The catheter body 110 includes a catheter liner 202 having a catheter lumen 204 extending therein (e.g., the catheter liner 202 defines the catheter lumen 204). The catheter lumen 204 is sized and shaped to receive a variety of instruments, fluids or the like. In one option, the catheter lumen 204 extends through the catheter body 110 to the handle assembly 150 (FIG. 1). The distal end of the catheter liner 202 forms at least a portion of the deflectable distal end portion 102. The catheter liner 202 includes, but is not limited to, flexible materials with sufficient strength and wear resistance for use in the catheter assembly 100. In one example, the catheter liner 202 includes a polymer such as polytetrafluoroethylene used under the trademark TEFLON® registered to E.I. Du Pont De Nemours and Company.

A flexible element duct 206 is positioned along the catheter liner 202, in one option. The flexible element duct 206 is substantially parallel to the catheter liner 202 and extends along at least a portion of the catheter liner 202, in another option. For instance, as shown in FIG. 2, the flexible element duct 206 extends from an intermediate portion 207 of the catheter body 110 (e.g., proximal to the deflectable distal end portion 102) toward the proximal end 106 adjacent to the handle assembly 150 (FIGS. 1A, B, C). In another example, the distal end 208 of the flexible element duct 206 is proximal to a distal tip 210 of the catheter body 110. The flexible element duct 206 includes an actuator lumen sized and shaped to receive the flexible element 200 (e.g., the flexible element duct 206 defines the actuator lumen). In one option, the flexible element 200 is slidably coupled with the flexible element duct 206 to facilitate transmission of pushing and pulling forces for deflection of the deflectable distal end portion 102.

In one option, a distal portion 201 of the flexible element 200 extends from the distal end 208 of the flexible element duct 206 toward the distal tip 210 of the catheter body 110. In another option, the flexible element distal portion 201 extends from the distal end 208 of the duct 206 toward a marker band 212. The marker band 212 extends around the catheter liner 202. Optionally, the marker band 212 is coupled to the catheter liner 202 with crimping, adhesives, overmolding or the like. The marker band 212 is fluoroscopic in still another option, facilitating viewing of the deflectable catheter distal end portion 102 during procedures (e.g., when the catheter body 110 is within vasculature). As shown in one example of the catheter body 110 in FIG. 2, the flexible element distal portion 201 is optionally coupled to the marker band 212. The distal portion 201 and the marker band 212 are coupled together with, but not limited to, welds, adhesives, mechanical fasteners or the like.

The catheter liner 202, flexible element duct 206, flexible element 200, and the marker band 212 are surrounded by an encapsulant 214. In one option, the encapsulant 214 includes a biocompatible metal, polymer and the like. In one example, the encapsulant 214 includes a poly-ether-block amide compound such as PEBAX® a trademark registered to the Atofina Corporation. The components of the catheter body 110 are encapsulated with the encapsulant 214, optionally, by heating the encapsulant to a molten state and squeezing it around catheter liner 202, flexible element duct 206, flexible element 200 and the marker band 212. The encapsulant 214 flows around the components, grasps them, and solidifies when cooled to form the catheter body 110. The encapsulant 214 forms a sidewall 215 and at least a portion of an outer surface 217 of the catheter body 110 surrounding the catheter lumen 204. At least the flexible element duct 206 and the flexible element 200 are contained within the encapsulant 214 and outside of the catheter lumen 204. The encapsulant 214 forms the outer surface 217 of at least a portion of the deflectable distal end portion 102, optionally. The encapsulant provides a smooth outer surface 217 and is easily positioned around the catheter body 110 (e.g., heated and squeezed around the catheter body 110). Complex manufacturing procedures including drilling and/or forming a pocket for an anchor and injecting an adhesive over the anchor are thereby avoided.

In another option, the encapsulant 214 is squeezed around the catheter liner 202 and the other components with shrink tubing 216. The shrink tubing 216 contracts when exposed to heat and squeezes the molten encapsulant 214 around the catheter liner 202 and the other components. The shrink tubing 216 ensures the encapsulant 214 provides a smooth consistent cross-sectional geometry for the catheter body 110. Optionally, the shrink tubing 216 is constructed with, but not limited to, polymers, such as Fluoro Ethylene Propylene. In yet another option, the shrink tubing 216 is split and removed from the catheter body 110 after the encapsulant 214 has solidified. As shown in FIG. 2, the shrink tubing 216 remains coupled around the encapsulant 214.

Optionally, the catheter body 110 includes a stiffening member embedded within the encapsulant, such as a braided member 218. In one option, the braided member 218 includes a stainless steel braid. The stiffening member facilitates rotation of the deflectable distal end portion 102 from the proximal end 106. Additionally the stiffening member also assists in preventing the catheter body 110 from collapsing. In another option, the stiffening member extends from the proximal end 106 to the deflectable distal end portion 102. The stiffening member extends form the proximal end 106 to the intermediate portion 207 of the catheter body 110, in yet another option. In this option, at least a portion of the deflectable distal end portion 102 is free of the stiffening member thereby enhancing the deflection capability of the distal end portion 102.

FIG. 2 illustrates one example of an anchor, such as a skirt 220 disposed around the distal portion 201 of the flexible element 200. The skirt 220 is a separate feature from the marker band 212. Optionally, the skirt 220 is proximal relative to the marker band 212. The skirt 220, in one option, is integral to the flexible element 200. In another option, the skirt 220 is coupled to the flexible element 200, for example by crimping, disposing projections within recesses, overmolding or the like. The skirt 220 is thereby substantially immobilized along the flexible element 200. In yet another option, the skirt 220 partially extends around the flexible element distal portion 201. In one example, the skirt 220 extends around the flexible element distal portion 201 approximately 180 degrees. In another example, the skirt 220 extends further (e.g., all the way) or less around the flexible element distal portion 201.

The skirt 220 provides a larger profile along the flexible element 200 than the element 200 itself. The profile of the skirt 220 allows the encapsulant 214 to grasp the skirt 220 and thereby easily couple with the flexible element distal portion 201 to allow transmission of pushing and pulling forces to the deflectable distal end portion 102. The skirt 220 anchors the flexible element distal portion 201 within the encapsulant 214. Pushing and pulling forces are thereby transmitted from the skirt 220 through the encapsulant 214 and to the catheter liner 202 facilitating deflection of the deflectable distal end portion 102. The encapsulant 214 forms the outer surface 217 of at least a portion of the deflectable distal end portion 102, optionally. In yet another option, the encapsulant 214 forms the sidewall 215 of the deflectable distal end portion 102 and the skirt 220 is retained within the sidewall 215 and adjacent to the outer surface 217. Positioning the skirt 220 within the sidewall 215 and adjacent to the outer surface 217 allows for an increased moment to be applied for deflection of the deflectable distal end portion 102 because the skirt 220 and the flexible element distal portion 201 are positioned remotely from the longitudinal center of the catheter body 110. Additionally, in still another option, the skirt 220 is fully encapsulated to further enhance transmission of pushing and pulling forces to the deflectable distal end portion 102. Further, the skirt 220 is retained along the catheter body 110, in an option, thereby allowing the distal tip 210 to have an atraumatic (i.e., deformable) surface for engaging with vasculature and organs.

As shown in FIGS. 4-8, the skirt 220 includes, optionally, additional features (e.g., knurling, projections, grooves, or the like) to further enhance the engagement of the skirt 220 with the encapsulant 214. In still another option, the skirt 220 is coupled to the catheter liner 202 with adhesives, mechanical fasteners, or the like, thereby facilitating transmission of pushing and pulling forces to the deflectable distal end portion 102.

In another option, where the catheter body includes the marker band 212, as shown in FIG. 2, the encapsulant grasps the skirt 220, the marker band 212 and the catheter liner 202. The pushing and pulling forces from the flexible element 200 are transmitted in part from the skirt 220 to the encapsulant 214 and the catheter liner 202 to deflect the catheter body 110. Additionally, pushing and pulling forces are transmitted from the flexible element 200 to the marker band 212, and from the marker band 212 to the encapsulant 214 and the catheter liner 202. In this example, the skirt 220 acts as a supplementary anchor to the marker band 202 and distributes the pushing and pulling forces between the skirt 220 and the marker band 212. This decreases the stresses on the coupling between the marker band 212 and the flexible element distal portion 201 and substantially prevents failure of the flexible element distal portion 201 adjacent to the marker band 212 (e.g., the region of the flexible element that is annealed from a weld or other treatment that weakens the element). Because the skirt 220 is proximal relative to the marker band 212, the skirt 220 substantially prevents puncturing of the catheter body 110 with a fractured flexible element 200 that fails near the marker band 212 (e.g., where the element 200 is annealed adjacent a weld or other means of coupling between the element 200 and the marker band 212). The skirt 220 transmits pushing forces to the deflectable distal end portion 102 and substantially prevents longitudinal movement of the fractured flexible element 200 that could otherwise puncture the catheter body 110 and cause injury to surrounding vasculature. Additionally, the skirt 220 allows for at least limited deflection of the catheter body 110 after fracture, facilitating completion of a procedure or removal of the catheter body 110 from vasculature. Moreover, the skirt 220 provides a profile that is localized around the flexible element 200 to minimize shearing stresses on the skirt 220 and enhance the lifespan of the skirt 220 while facilitating deflection of the deflectable distal end portion 102 and immobilization of a fractured flexible element.

Figure 3:
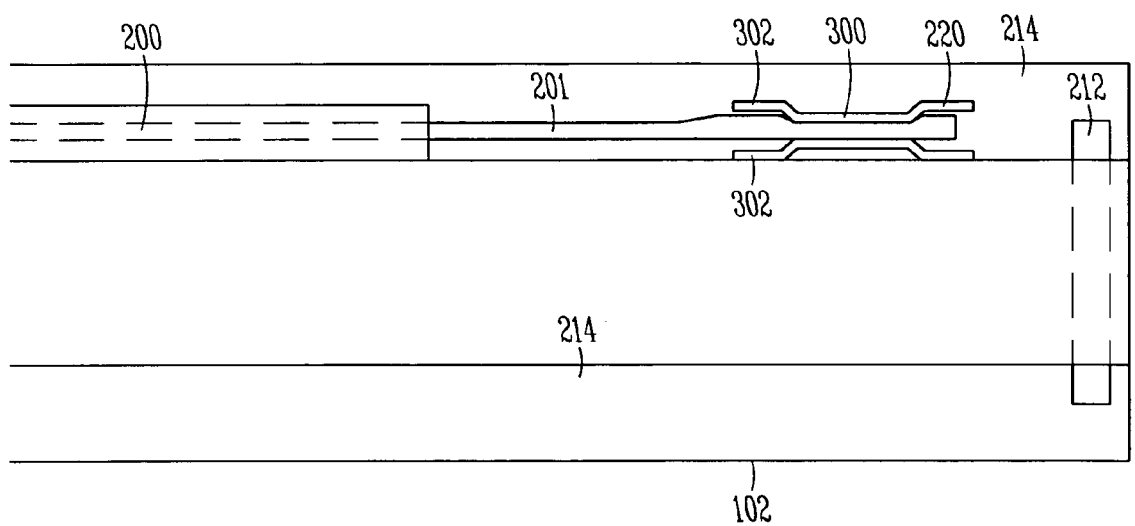
FIG. 3 is a cross-sectional view of one example of a catheter assembly.

FIG. 3 shows one example of the skirt 220 coupled along the flexible element distal portion 201. The skirt 220 is at least partially surrounded by the encapsulant 214 and substantially immobilized in the encapsulant 214. Similar to the example shown in FIG. 2, the skirt 220 cooperates with the encapsulant 214 to couple the flexible element distal portion 201 to the deflectable distal end portion 102. The marker band 212 is encapsulated as well, but not otherwise coupled to the flexible element 200. The skirt 220 is a separate feature from the marker band 212, and relatively proximal to the band 212. Pushing and pulling forces are thereby transmitted through the skirt 220 to the encapsulant 214 to deflect the distal end portion 102 as shown in FIGS. 1A, C.

The skirt 220, shown in FIG. 3, is constructed with a deformable material, for instance metals, such as steel, aluminum or the like. In one option, the skirt 220 acts as a clamp and is deformed around the flexible element distal portion 201 by crimping. The skirt 220 includes a crimped portion 300 that engages against the flexible element distal portion 201 and couples the skirt 220 to the distal portion 201. Crimping the skirt 220 to the distal portion 201 substantially immobilizes the skirt 220 relative to the flexible element 200. Crimping the skirt 220 around the flexible element distal portion 201 substantially reduces the likelihood of fracturing the flexible element 200 with pushing and pulling forces. The skirt 220 is not coupled to the flexible element 200 with a weld or other means, and therefore there is no weakened annealed region along the flexible element 200. The strength of the flexible element 200 (e.g., tensile and compression strengths) is thereby consistently maintained along the length of the flexible element 200. The skirt 220 and the flexible element 200 have tension and compression strengths at least as great as the tension and compression strengths of the encapsulant 214 and thereby substantially reduce fracture of the flexible element 200. Optionally, the catheter body 110 (FIGS. 1A-C and 2) is adapted to fail before failure of the flexible element 200 and the skirt 220, thereby substantially preventing puncture of the catheter body 110 by a fractured flexible element 200. In another option, the skirt 220 includes metals, polymers and the like. Optionally, the skirt 220 is coupled to the flexible element distal portion 201 with adhesives, overmolding and the like.

The skirt 220 includes projections 302, for instance non-crimped segments of the skirt 220, sized and shaped to extend from the flexible element distal portion 201. The projections 302 are securely grasped by the encapsulant 214 and anchored therein to firmly couple the skirt 220 and the flexible element 200 to the deflectable distal end portion 102. In one example, as shown in FIG. 3, the encapsulant 214 fills a space defined by the projections 302 to firmly anchor the skirt within the encapsulant. For instance, the projections 302 form a flared conical geometry extending away from the crimped portion 300 of the skirt 220 that receives the encapsulant therein. Pushing and pulling forces are transmitted from the flexible element 200 to the skirt 220 and the projections 302 are securely grasped by the encapsulant 214. The pushing and pulling forces are transmitted from the skirt 220 and the projections 302 through the encapsulant 214 to the deflectable distal end portion 102. The skirt 220 thereby pushes and pulls the deflectable distal end portion 102 to deflect the distal end portion 102 as desired.

Figure 4A:
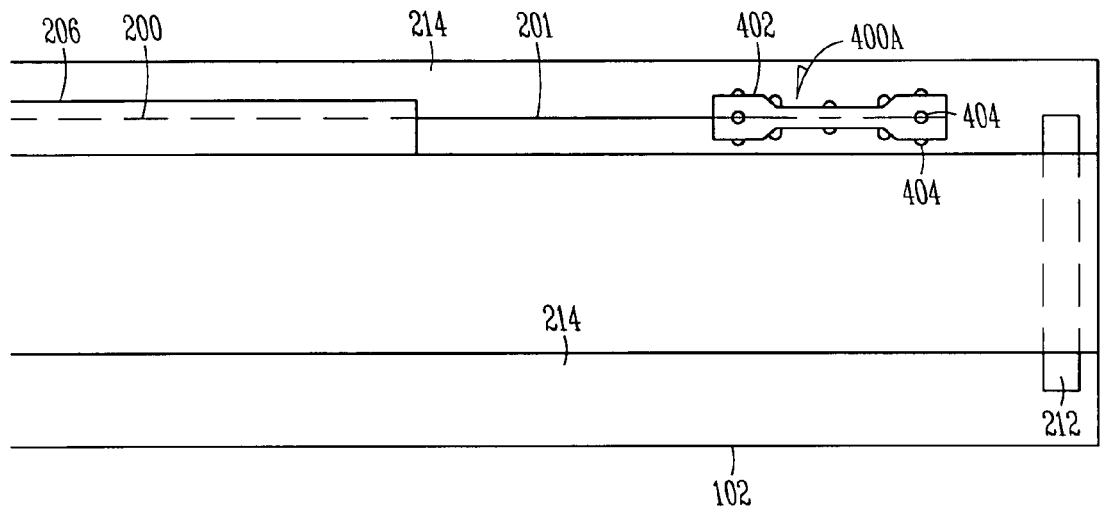
FIG. 4A is a partial sectional view of another example of a catheter assembly.

FIGS. 4A, B, D illustrate examples of skirts 400A, B, D coupled around the flexible element distal portion 201 extending outside the flexible element duct 206. In one option, the skirts 400A, B, D are integral to the flexible element distal portion 201. In another option, the skirts 400A, B, C are coupled to the distal portion 201 of the flexible element 200 by crimping, adhesives, overmolding or the like. Where the skirts 400A, B, D are crimped along the flexible element distal portion 201, the skirts 400A, B, D are crimped in a similar manner as skirt 220 (FIG. 2).

The skirt 400A shown in FIG. 4A has an outer surface 402 including surface roughening, texturing, features or the like, such as knurling 404. The knurling 404 provides additional features for the encapsulant 214 to grasp and firmly anchor the skirt 400A to the deflectable distal end portion 102. The knurling 404 assists in substantially immobilizing the skirt 400A within the encapsulant 214. Pushing and pulling forces are thereby readily transmitted through the skirt 400A to deflect the distal end portion 102 through the encapsulant 214. In one option, where the flexible element distal portion 201 is welded to the marker band 212 (FIG. 2), the knurling 404 enhances the immobilization of the skirt 400A and assists in substantially preventing a fractured flexible element 200 from puncturing the catheter body 110 (FIG. 1).

The knurling 404 is formed along the skirt 400A by molding, crimping, or the like. In one option, the knurling 404 along the skirt 400A is formed with a crimping tool having a working surface with corresponding recesses. When the skirt 400A is crimped with the tool the skirt outer surface 402 assumes a configuration corresponding to the crimping tool (i.e., the knurling 404 is in a pattern corresponding to the recesses). In one option, the knurling 404 is formed on the skirt 400A without crimping the skirt 400A to the flexible element distal portion 201. In another option, the skirt 400A is crimped around the distal portion 201 after forming the knurling 404. The skirt 400A is adhered, overmolded or the like to couple the skirt 400A to the distal portion 201, in yet another option. The knurling 404 is formed on the skirt 400A and the skirt is crimped around the distal portion 201 in one step, optionally.

Figure 4B:
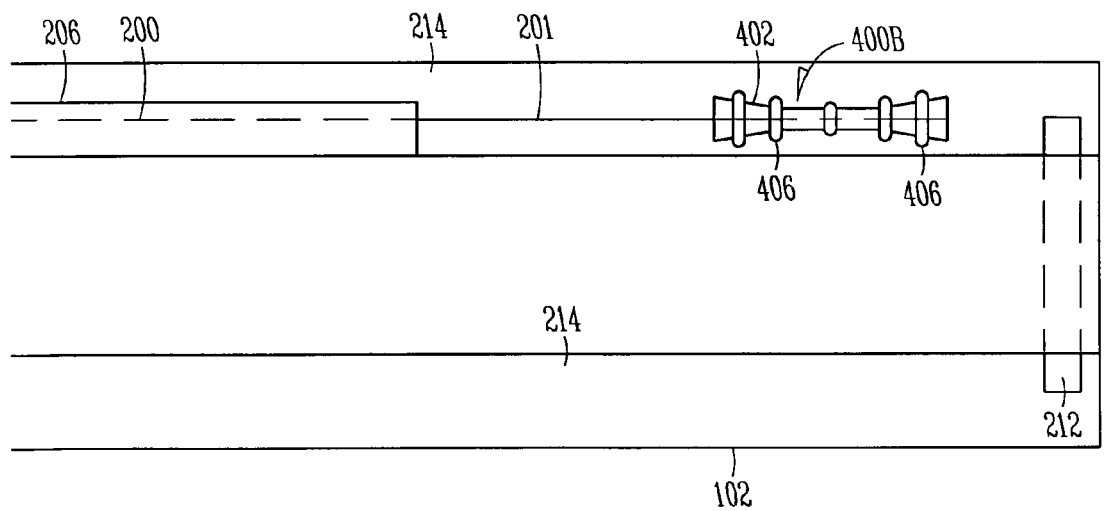
FIG. 4B is a partial sectional view of another example of a catheter assembly.

FIG. 4B illustrates a skirt 400B similar in some respects the skirt 400A shown in FIG. 4A. Skirt 400B includes ridges 406 formed along the outer surface 402 of the skirt 400B. As with the knurling 404 (FIG. 4A), the ridges 406 provide additional features for the encapsulant 214 to grasp and firmly anchor the skirt 400B to the deflectable distal end portion 102. Optionally, where the flexible element 200 is welded to the marker band 212, the ridges 406 enhance the immobilization of the skirt 400B and assist in substantially preventing a fractured flexible element from puncturing the catheter body 110 (See FIG. 2). In one option, the ridges 406 are formed along the skirt 400B by molding, crimping, or the like. In another option, the skirt 400B is crimped adhered, overmolded or the like to couple the skirt 400B to the flexible element 200.

Figure 4C:
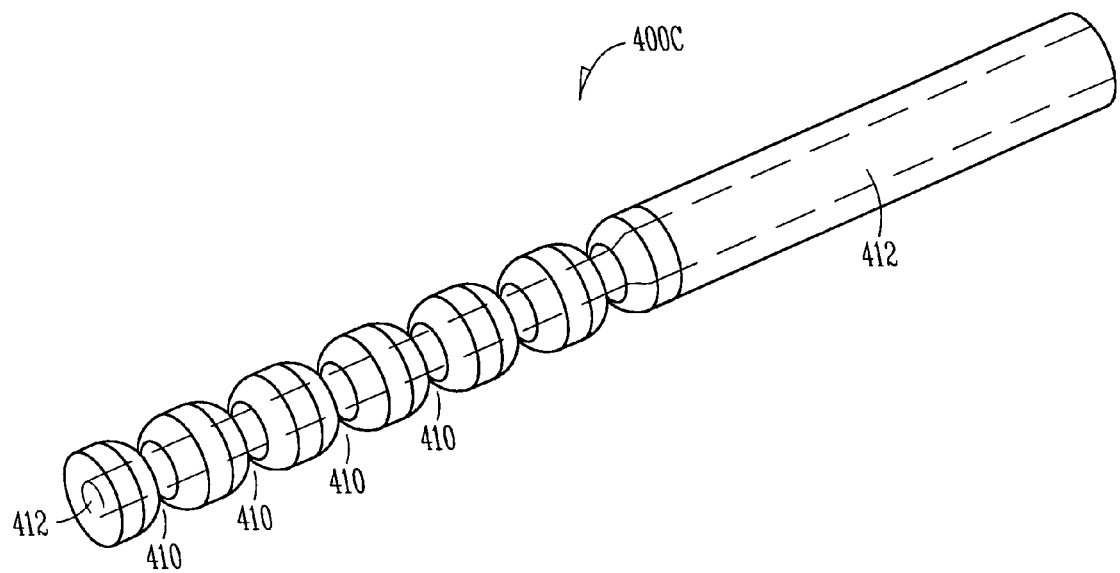
FIG. 4C is a perspective view of one example of an anchor.

FIG. 4C illustrates a skirt 400C including recesses, for instance, corrugations 410. The corrugations 410 provide features for the encapsulant 214 (FIG. 2) to flow into and enhance the grasp of the encapsulant on the skirt 400C. The encapsulant 214 and the skirt 400C cooperate to anchor the flexible element distal portion 201 (FIG. 2) in the deflectable distal end portion 102 (FIG. 2). The skirt 400C, in one option, has an annular shape as shown in FIG. 4C and the corrugations 410 extend around the annular perimeter of the skirt 400C. The corrugations 410 facilitate transmission of pushing and pulling forces through the skirt 400C to the encapsulant 214 to deflect the distal end portion 102.

The skirt 400C is stamped, in one option, to create the corrugations 410. In another option, the skirt 400C is formed with the corrugations 410 prior to crimping the skirt 400C to the flexible element distal portion 201 (FIG. 2). The skirt 400C includes a flexible element lumen 412. In one option, the flexible element distal portion 201 is inserted into a non-corrugated portion 412 of the skirt 400C and the non-corrugated portion 412 is crimped to couple the skirt 400C with the distal portion 201. In another option, the flexible element distal portion 201 is inserted into the flexible element lumen 412 and the skirt 400C is stamped to form the corrugations 410 and couple the skirt 400C to the flexible element distal portion 201. In yet another option, the flexible element distal portion 201 extends through the skirt 400C and is welded to the marker band 212 (FIG. 2). The corrugations 410 increase the immobilization of the skirt 400C and substantially prevent fracturing of the flexible element 200 (FIG. 2). The skirt 400C prevents a fractured flexible element 200 from puncturing the catheter body 110.

Figure 4D:
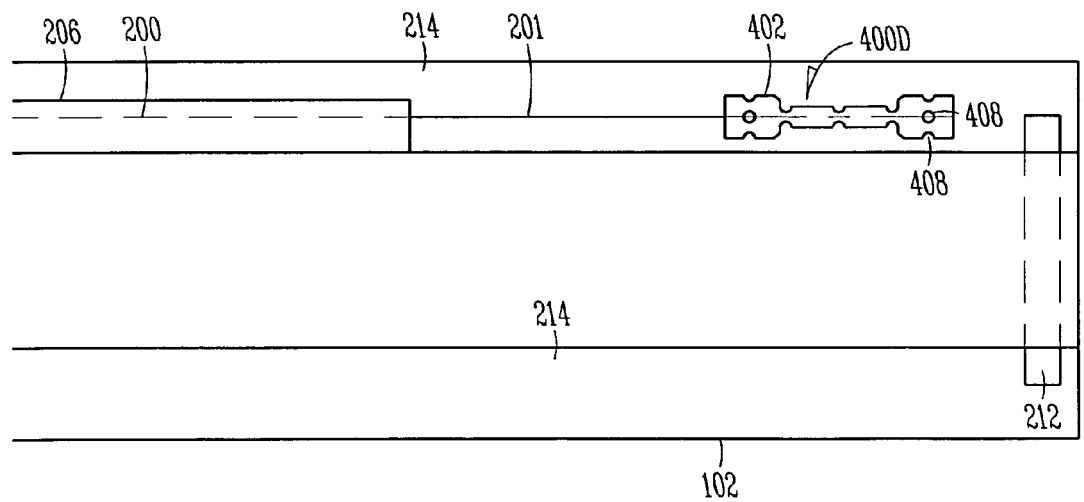
FIG. 4D is a partial sectional view of another example of a catheter assembly.

FIG. 4D illustrates a skirt 400D. The outer surface 402 of the skirt 400D includes recesses 408. The recesses 408 provide additional features for the encapsulant 214 to flow into and firmly anchor the skirt 400D to the deflectable distal end portion 102. The recesses 408 thereby enhance transmission of pushing and pulling forces through the skirt 400D to deflect the distal end portion 102. Additionally, where the flexible element distal portion 201 is welded to the marker band 212 (FIG. 2) in one option, the recesses 408 increase the immobilization of the skirt 400D and substantially prevent a fractured flexible element from puncturing the catheter body 110 (FIG. 2). Optionally, the recesses 408 include openings extending through the skirt 400D.

The recesses 408 are formed along the skirt 400D by molding, crimping, stamping, drilling, etching, or the like. In one option, the recesses 408 along the skirt 400D are formed with a crimping tool having a working surface with bosses corresponding to the pattern of the recesses 408. When the skirt 400D is crimped with the tool the skirt outer surface 402 assumes a configuration corresponding to the crimping tool (i.e., the recesses 408 are in a pattern corresponding to the bosses). As described above for the skirt 400A, optionally, the skirt 400D is crimped to form the recesses 408 and couple the skirt 400D to the flexible element distal portion 201. In another option, the skirt 400D is crimped to form the recesses 408 and crimped again to couple the skirt 400D to the flexible element 200. In yet another option, the skirt 400D is adhered, overmolded or the like to couple the skirt 400D to the flexible element 200.

Figure 5A:
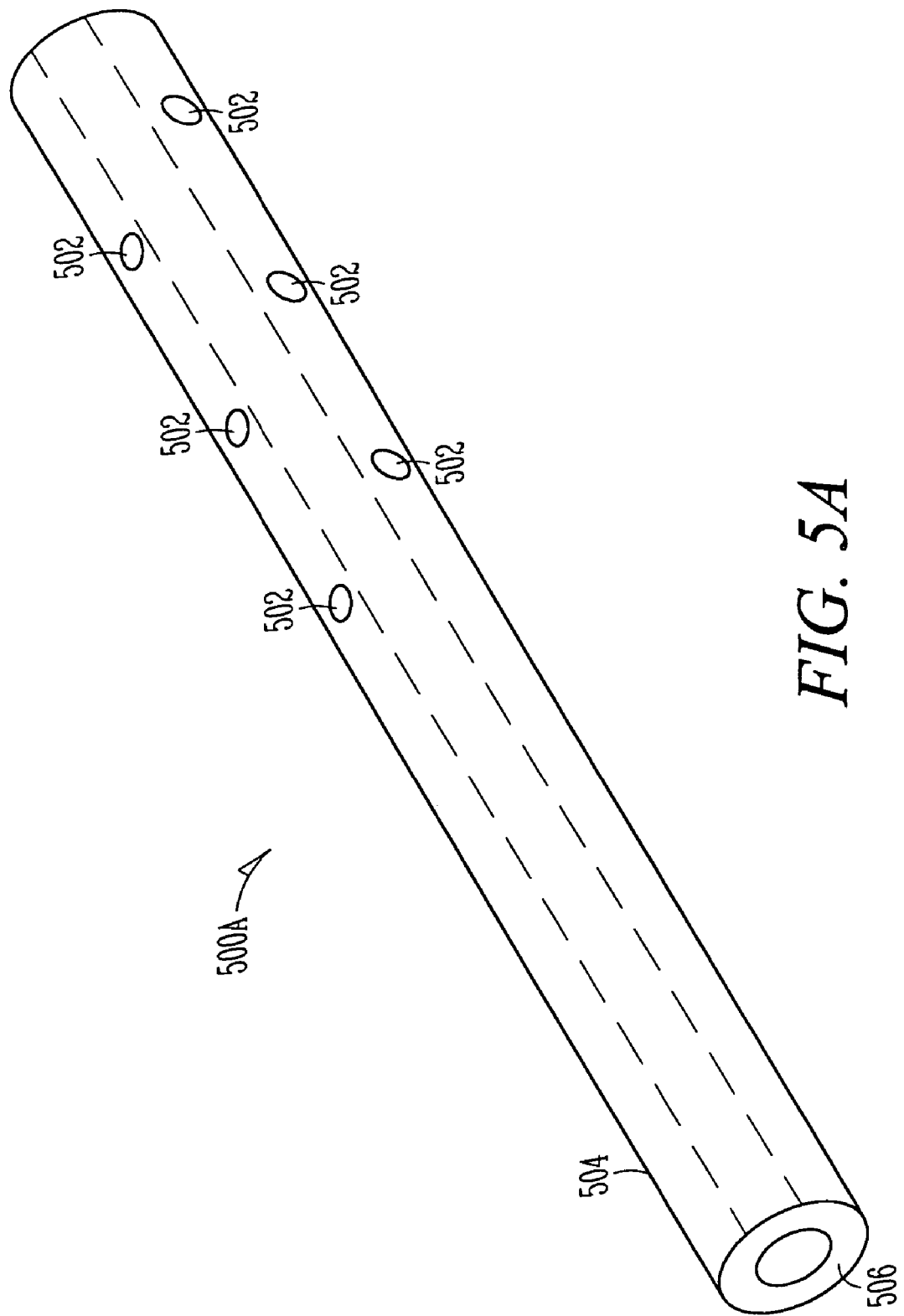
FIG. 5A is a perspective view of another example of an anchor.
Figure 5B:
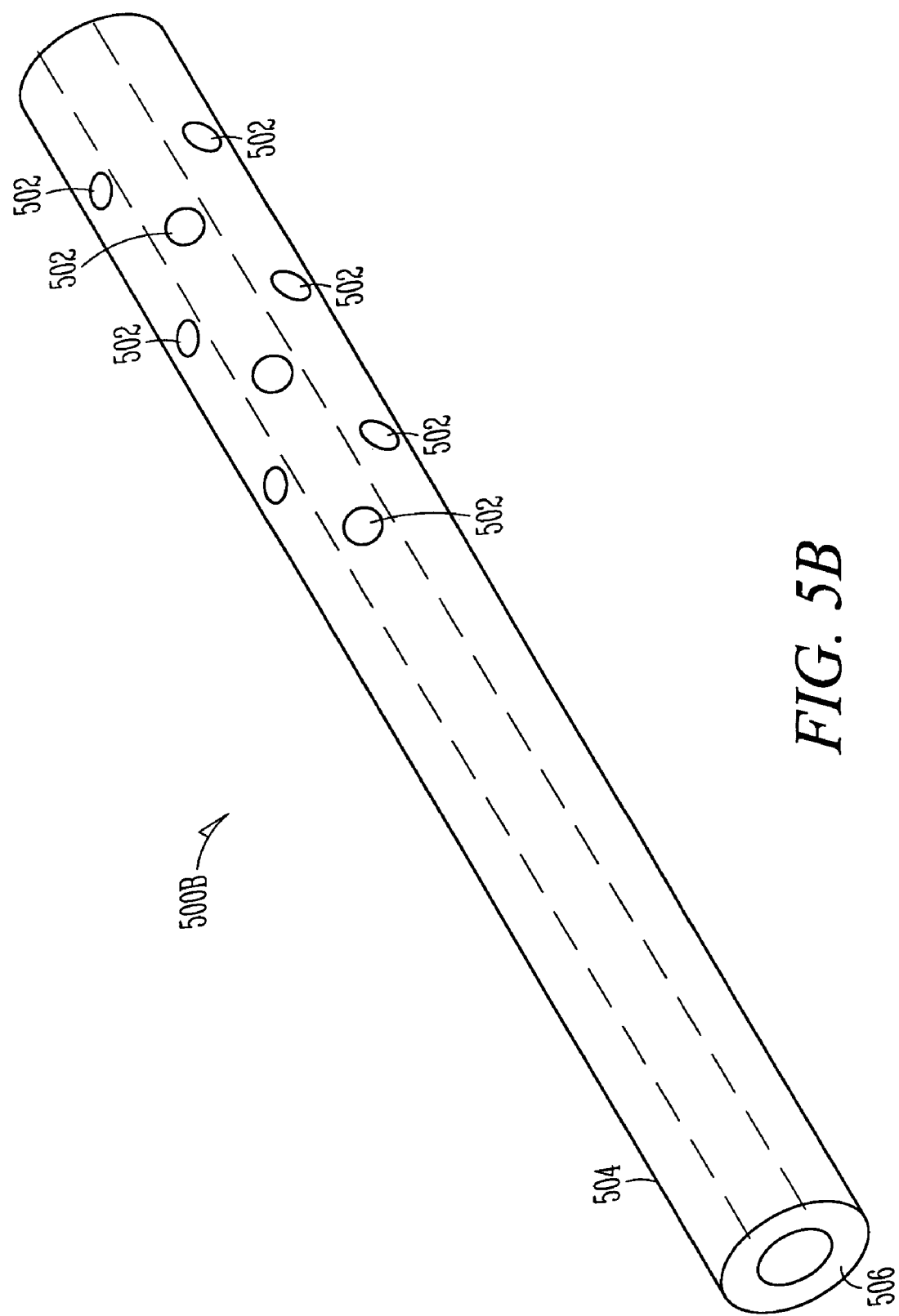
FIG. 5B is a perspective view of yet another example of an anchor.

FIGS. 5A, B show examples of skirts 500A, B including recesses 502 dimensioned and configured to receive encapsulant 214 (FIG. 2). Referring now to FIG. 5A, during forming of the deflectable distal end portion 102 (FIG. 1) the encapsulant 214 flows into the recesses 502 and immobilizes the skirt 500A within the encapsulant 214. The recesses 502 allow the encapsulant 214 to grasp the skirt 500A and facilitate transmission of pushing and pulling forces to the deflectable distal end portion 102. In one option, the recesses 502 are formed by drilling holes in a pattern along a portion of the skirt 500A. Optionally, the recesses 502 are formed by stamping, etching or the like. As shown in FIG. 5B, additional recesses 502 are formed in the skirt 500B. The larger number of recesses 502 allow for additional penetration of the encapsulant 214 (FIG. 2) and enhance the immobilization of the skirt 500B.

The skirt 500A is coupled to the flexible element distal portion 201 (FIG. 2) by inserting the flexible element distal portion 201 at least partially through a flexible element lumen 506. In one option, a portion 504 of the skirt 500A, which does not have recesses, is crimped around the flexible element distal portion 201. Crimping the portion 504 provides a strong coupling between the skirt 500A and the flexible element distal portion 201. In another option, the entire skirt 500A is crimped around the flexible element distal portion 201. The skirt 500A is coupled with the flexible element distal portion 201 so the portion 504 is proximal relative to the recesses 502 and the distal tip 210 of the catheter body 110 (FIG. 1), optionally. In still another option, the skirt 500A is coupled so the recesses 502 are proximal relative to the distal tip 210 and the non-recessed portion 504. The skirt 500B, shown in FIG. 5B, is coupled to the flexible element distal portion 201 in a similar manner as described above. The skirts 500A, B are constructed with, but not limited to metals, in one option. For instance, the skirts 500A, B include stainless steel.

Figure 6:
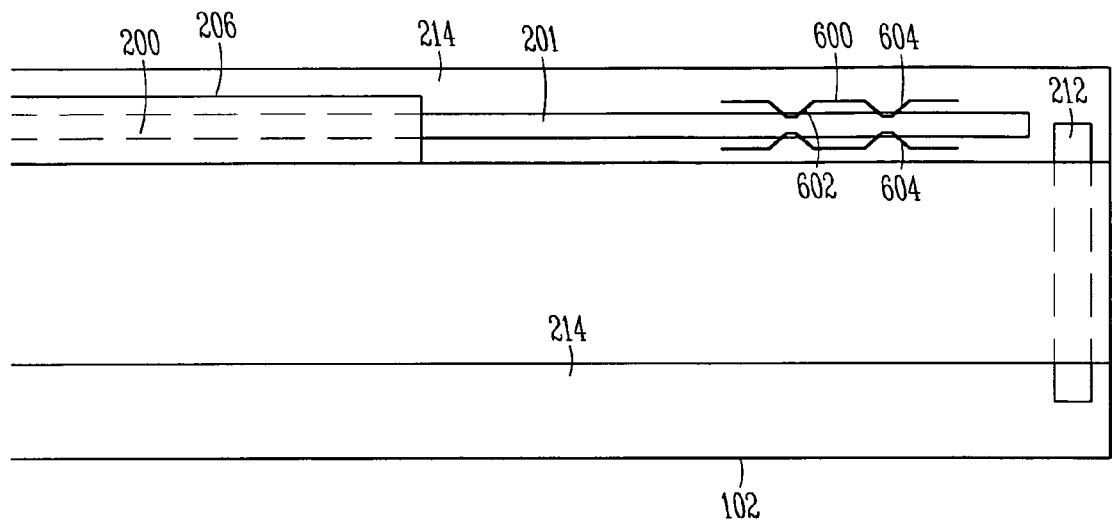
FIG. 6 is a cross-sectional view of yet another example of a catheter assembly.

FIG. 6 shows another example of a skirt 600 embedded within the encapsulant 214. In the example shown in FIG. 6, the deflectable distal end portion 102 includes the distal portion 201 of the flexible element 200 extending from the flexible element duct 206. The skirt 600 is coupled along the flexible element distal portion 201. As shown, the flexible element distal portion 201 is not coupled with the marker band 212. In another option, the distal portion 201 is coupled to the marker band 212 (FIG. 2), for instance, with a weld.

The skirt 600 acts as a clamp and is deformable. In one option, the skirt 600 includes, but is not limited to, metals such as steel, aluminum or the like. In another option, the skirt 600 extends part way around the distal portion 201 of the flexible element 200. The skirt 600 extends fully around the distal portion 201, in yet another option. Prior to coupling the skirt 600 with the flexible element distal portion 201, the skirt 600 has an inner surface 602 sized and shaped to fit around the flexible element 200 and allow positioning of the skirt 600 along the element 200. Optionally, the inner surface 602 has a substantially cylindrical geometry prior to coupling of the skirt 600 to the flexible element 200.

In one option, the skirt 600 is positioned along the flexible element distal portion 201 and deformed (e.g., crimped) to engage against the distal portion 201. The skirt 600 is thereby substantially immobilized along the flexible element 200. As shown in FIG. 6, the skirt 600 is deformed at a discrete point to create at least one projection, such as spur 604. In the example shown in FIG. 6, the skirt 600 is deformed to include four spurs 604. The spurs 604 engage the inner surface 602 of the skirt 600 with the flexible element distal portion 201. Optionally, the flexible element distal portion 201 includes projections and the inner surface 602 of the skirt 600 is crimped over the projections to couple the skirt to the distal portion 201.

In another option, the spurs 604 extend into the flexible element 200 and deform the flexible element 600 to define corresponding recesses sized and shaped to receive the spurs 604. Optionally, the spurs 604 extend between individual filars of the flexible element 200 (e.g., a wire with a plurality of steel filars). The spurs 604 immobilize the skirt 600 along the flexible element 200 without substantially weakening the flexible element 200. Additionally, the spurs 604 allow the skirt 600 to have a substantially enlarged uncrimped profile while only a small portion of the skirt 600 is narrowed to form the spurs 600. When coupled to the flexible element 200 with the spurs 604, the skirt 600 has a larger profile and improved anchoring within the encapsulant 214. In another option, the skirt 600 includes additional features, such as knurling, ridges, recesses or the like, as previously described. These additional features provide an even larger profile for the encapsulant 214 to grasp and anchor the skirt 600, further enhancing transmission of pushing and pulling to the deflectable distal end portion 102. In another option, where the flexible element distal portion 201 is coupled to a marker band 212 (FIG. 2), the skirt 600 substantially prevents puncturing of the catheter body 110 if the flexible element 200 fractures adjacent to the marker band 212.

Figure 7:
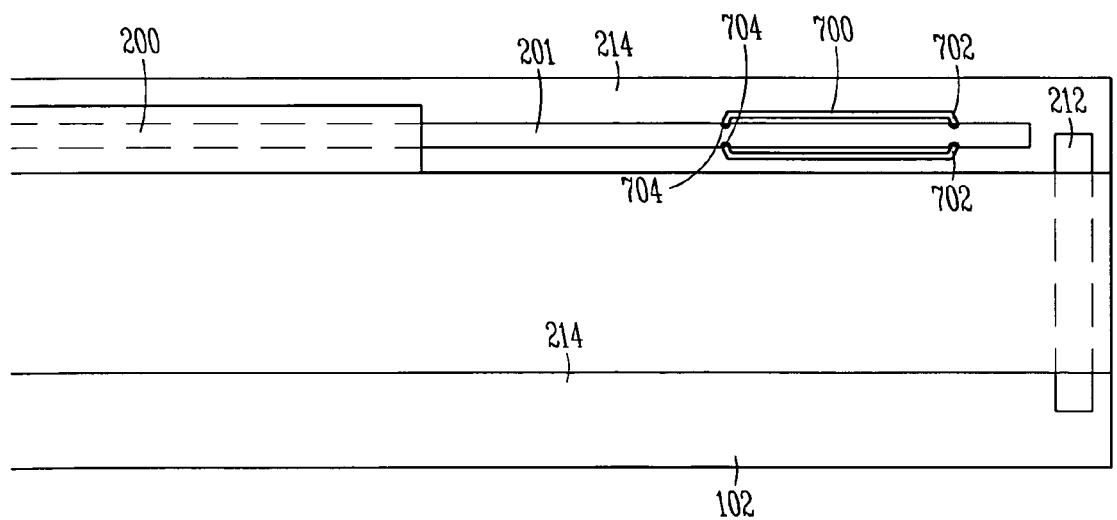
FIG. 7 is a cross-sectional view of still another example of a catheter assembly.

FIG. 7 shows yet another example of a skirt 700 coupled along the distal portion 201 of the flexible element 200. In one option, the flexible element distal portion 201 is free of welds and is not coupled with the marker band 212. In another option, the flexible element distal portion 201 is coupled to the marker band 212 (See FIG. 2) distally relative to the skirt 700. The distal portion 201 is optionally welded to the marker band 212.

In one option, the skirt 700 acts as a clamp and is deformable to engage against the flexible element distal portion 201. As described above, the skirt 700 includes, but is not limited to, metals such as steel, aluminum or the like. In another option, the skirt 700 is overmolded around the flexible element distal portion 201 to couple the skirt 700 to the flexible element 200. The skirt 700 includes, for instance, but is not limited to metals, polymers or the like. Optionally, the skirt 700 extends part way around the flexible element distal portion 201. The skirt 700 extends fully around the distal portion 201, in another option.

As shown in FIG. 7, the skirt 700 includes projections 702 sized and shaped to fit within recesses 704 formed in the flexible element distal portion 201. In one option, the ends of the skirt 700 are crimped to form the projections 702. The projections 702 engage the distal portion 201 and form the recesses 704. In another option, the recesses 704 are preformed in the flexible element distal portion 201 and the projections 702 are positioned within the recesses 704 to engage the skirt 700 to the distal portion 201. The recesses are formed, optionally, by deformation of the flexible element, etching, drilling or the like. In yet another option, the skirt 700 includes recesses and the flexible element distal portion 201 includes projections sized and shaped to fit within the recesses.

When coupled to the flexible element distal portion 201, the skirt 700 is substantially immobilized along the flexible element 200. The skirt 700 provides an enlarged profile for the flexible element distal portion 201 and facilitates grasping of the flexible element 200 by the encapsulant 214. Optionally, the skirt 700 includes additional features, such as knurling, ridges, recess or the like, as described above. Additional features present an even larger profile for the encapsulant 214 to anchor the skirt 700, further enhancing transmission of pushing and pulling to the deflectable distal end portion 102 through the encapsulant 214. In another option, where the flexible element distal portion 201 is coupled to a marker band 212 (FIG. 2), the skirt 700 substantially prevents puncturing of the catheter body 110 if the flexible element 200 fractures adjacent to the marker band 212.

Figure 8A:
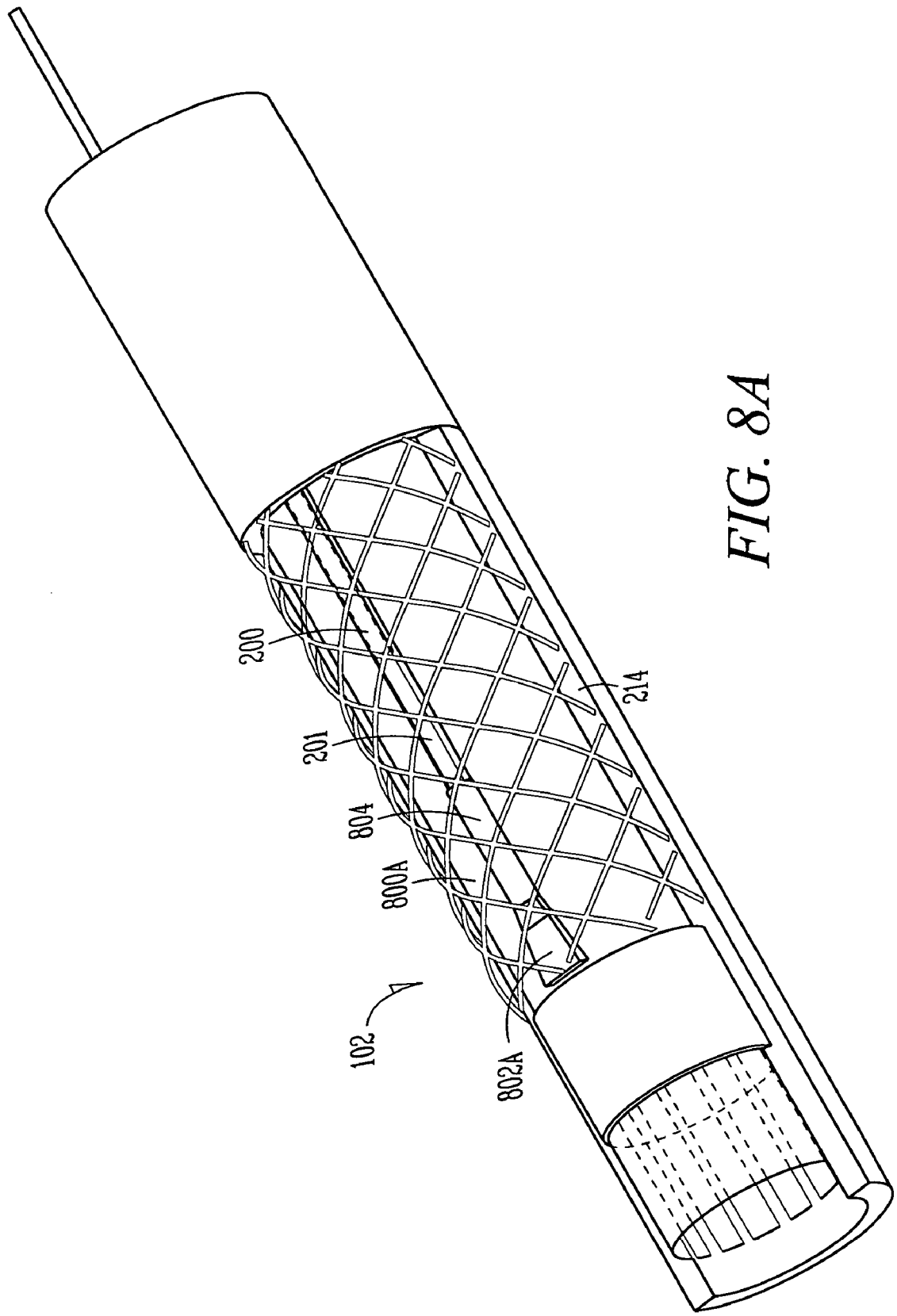
FIG. 8A is a perspective view of one example of a catheter assembly.

FIG. 8A shows one example of the deflectable distal end portion 102 including a skirt 800A having a flared portion 802A (e.g., a paddle geometry). FIGS. 8B, C, D show additional examples of skirts 800B, C, D with flared portions 802B, C, D having different geometries. Each of the flared portions 802A-D provide a large profile for the encapsulant 214 (FIG. 8A) to grasp and immobilize the skirts 800A-D. The skirts 800A-D provide improved transmission of pushing and pulling forces to the deflectable distal end portion 102. In another option, where the flexible element distal portion 201 is coupled to a marker band 212 (FIG. 2), the skirts 800A-D substantially immobilize the flexible element distal portion 201 to prevent puncturing of the catheter body 110 if the flexible element 200 fractures adjacent to the marker band 212. Optionally, the flared portions 802A-D are located distally relative to the flexible element distal portion 201. In another option, the flared portions 802A-D are coincident with the flexible element distal portion 201, for instance the tip of the distal portion is disposed within one of the flared portions 802A-D.

As shown in FIG. 8A, the skirt 800A includes a flared portion 802A and a proximal portion 804. The flared portion 802A provides a wide and flat profile extending outside of the profile of the proximal portion 804 to facilitate grasping by the encapsulant 214. The flared portion 802A is formed, in one option, by stamping the skirt 800A in the region distal to the proximal portion 804. In another option, the flared portion 802A is formed by molding, machining or the like. The skirt 800A is optionally stamped with a die that defines the geometry of the flared portion 802A. Other examples of flared portions are shown in FIGS. 8B, C, D. The flared portion 802B (FIG. 8B), in one option, is formed with a die that projects the flared portion 802B away from the proximal portion 804 with a curved geometry. In another option, the curved geometry complements the rounded geometry of the deflectable distal end portion 102. As shown in FIG. 8C, in yet another option, the skirt 800C is stamped with a die that projects the flared portion 802C further away from the proximal portion 804 than the flared portion 802B of skirt 800B. The flared portions 802B, C remain substantially adjacent to the proximal portion 804 to substantially minimize shearing of the flared portions 802B, C. Optionally, the skirts 800A-D are constructed with, but not limited to, deformable materials such as metals that maintain the geometries of the flared portions 802A-D. In one example, the skirts 800A-D include stainless steel.

In another option shown in FIG. 8D, the flared portion 802D is formed with a die that projects the flared portion 802D away from the proximal portion 804 and also forms at least one recess, such as corrugation 806. The corrugation 806 defines a non-annular feature for the flared portion 802D. The profile of the flared portion 802D including the added feature of the corrugation 806 enhances immobilization of the skirt 800D within the encapsulant (FIG. 8A). The flared portion 802D having the corrugation 806 transmits pushing and pulling forces to the deflectable distal end portion 102 (FIG. 8A).

Referring again to FIG. 8A, the proximal portion 804, in one option, extends substantially around the flexible element distal portion 201 and is crimped around the distal portion 201 to couple the skirt 800A with the flexible element 200. In another option, the proximal portion 804 extends part way around the flexible element distal portion 201 and is crimped to couple the skirt 800A with the flexible element 200. In a similar manner, the proximal portions 804 of the skirts 800B, C, D are crimped to couple the skirts with the flexible element 200, optionally. In yet another option, the skirts 800A-D are coupled with the flexible element with other means including, but not limited to, adhesives, molding or the like.

Figure 9:
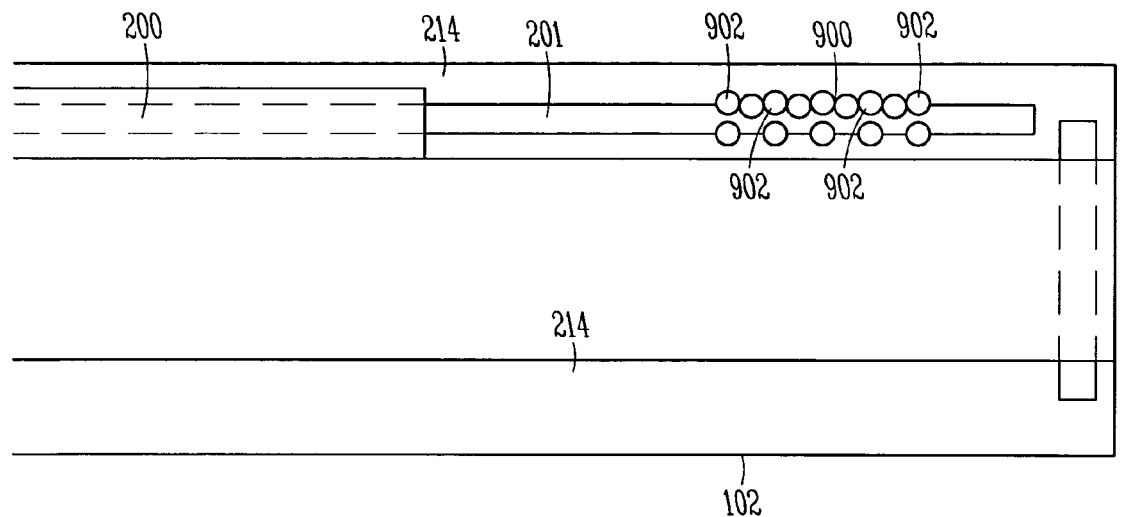
FIG. 9 is a cross-sectional view of one example of a catheter assembly.

A deflectable distal end portion 102 including a skirt 900 integral to the flexible element distal portion 201 is shown in FIG. 9. The skirt 900 includes features, such as knurling 902, provided to anchor the flexible element distal portion 201 within the encapsulant 214. In one option, the knurling 902 extends around the distal portion 201. In another option, the knurling 902 extends part way around the distal portion 201.

Optionally, the knurling 902 includes brazing dots formed with metals such as aluminum, copper and the like. The brazing dots are applied to the flexible element distal portion 201 by melting the brazing material and applying it as dots. The brazing dots cool and solidify to form the knurling 902. In another option, the flexible element 200 is molded, crimped or the like to form the knurling 902. Crimping the flexible element 200 compresses the element in one dimension while widening the element 200 in another dimension.

In a similar manner to the skirts 220, 400A-D, 500A, B, 600, 700 and 800A-D, the skirt 900 provides an enlarged profile for the flexible element distal portion 201 and facilitates grasping of the flexible element 200 by the encapsulant 214. The skirt 900 provides improved transmission of pushing and pulling forces to the deflectable distal end portion 102 through the encapsulant 214. In another option, where the flexible element distal portion 201 is coupled to a marker band 212 (FIG. 2), the skirt 900 substantially prevents puncturing of the catheter body 110 if the flexible element 200 fractures adjacent to the marker band 212.

Figure 10:
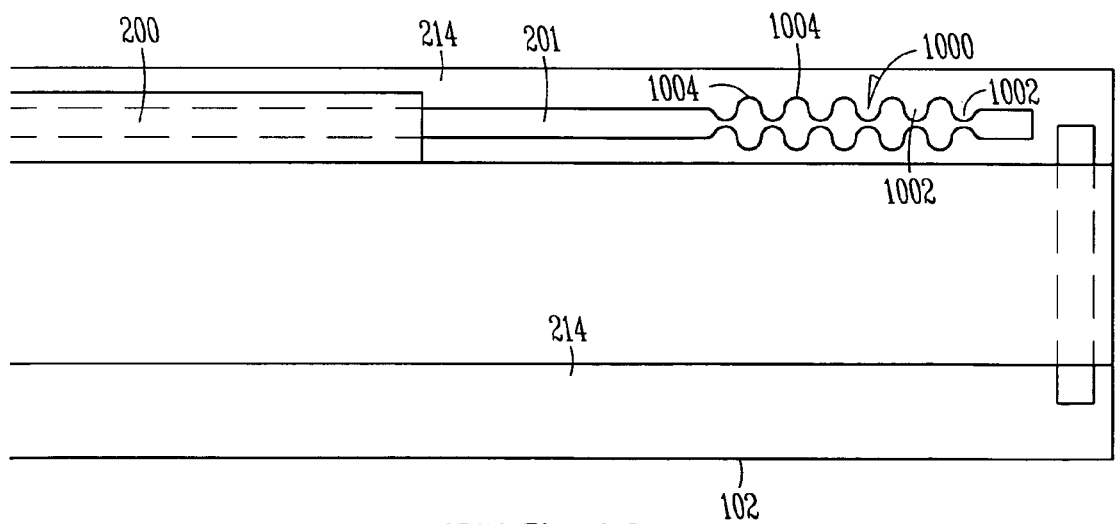
FIG. 10 is a cross-sectional view of another example of a catheter assembly.

FIG. 10 illustrates another example of a deflectable distal end portion 102 including a skirt 1000 integral to the flexible element distal portion 201. The skirt 1000 includes features, such as recesses 1002, provided to receive the encapsulant 214 and thereby anchor the flexible element distal portion 201 within the encapsulant 214. In one option, the skirt 1000 further includes flaring 1004 disposed between the recesses 1002 to improve the anchoring of the skirt 1000 within the encapsulant 214. Optionally, the recesses 1002 and/or flaring 1004 extend part way around the distal portion 201. The recesses 1002 and/or flaring 1004 extend all the way around the flexible element distal portion 201, in another option.

The recesses 1002 and flaring 1004 are formed, in one option, by crimping and deforming the flexible element distal portion 201. The recesses 1002 are formed by crimping, molding, etching or the like along the flexible element 200. The flaring 1004 is formed, in another option, by pulling the flexible element distal portion 201 radially to increase the circumference around the distal portion 201. Where the flexible element 200 includes multiple filars (e.g., steel filars), radially pulling on the element 200 pulls at least some of the filars outward to form the flaring 1004. Optionally, the flaring 1004 is formed as the flexible element 200 is longitudinally compressed along a portion of its length corresponding to the skirt 1000. The compression bows out the filars of the flexible element 200 to form the flaring 1004. In yet another option, the flaring 1004 and/or recesses 1002 are formed alone without the other of the flaring 1004 or the recesses 1002.

Similar to the examples described above, the skirt 1000 provides an enlarged profile for the flexible element distal portion 201 and facilitates grasping of the flexible element 200 by the encapsulant 214. The flaring 1004 and the recesses 1002 anchor the flexible element distal portion 201 within the encapsulant 214 to provide improved transmission of pushing and pulling forces to the deflectable distal end portion 102. In another option, where the flexible element distal portion 201 is coupled to a marker band 212 (FIG. 2), the skirt 1000 substantially prevents longitudinal movement of the flexible element distal portion 201 within the catheter body 110, for instance, if the flexible element 200 fractures adjacent to the marker band 212. Puncturing of the catheter body 110 is thereby substantially prevented by anchoring the skirt 1000 within the encapsulant of the deflectable distal end portion 102.

Figure 11:
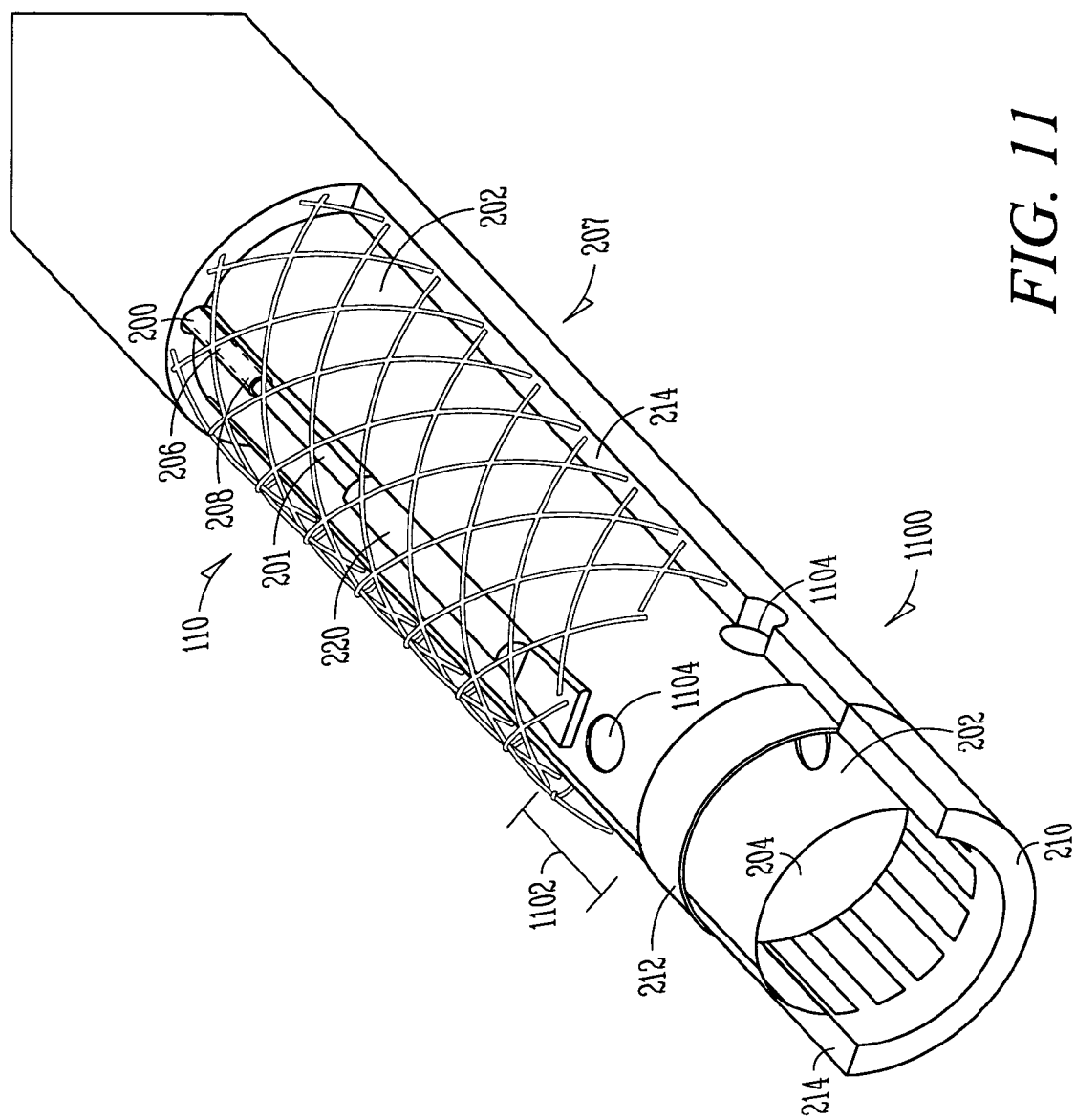
FIG. 11 is a partial sectional view of another example of the deflectable distal end portion.

FIG. 11 shows a partial cut-away of another example of a deflectable distal end portion 1100 of the catheter body 110 shown in FIGS. 1A, B, C. The deflectable distal end portion 1100 is similar in some respects to the deflectable distal end portion 102 shown in FIG. 2. The catheter body 110 includes a catheter liner 202 having a catheter lumen 204 extending therein. The distal end of the catheter liner 202 forms at least a portion of the deflectable distal end portion 1100. A flexible element duct 206 is positioned along the catheter liner 202, in one option. As shown in FIG. 11, the flexible element duct 206 extends from an intermediate portion 207 of the catheter body 110 (e.g., proximal to the deflectable distal end portion 102) toward the proximal end 106 adjacent to the handle assembly 150 (FIGS. 1A, B, C). In another example, the distal end 208 of the flexible element duct 206 is proximal to a distal tip 210 of the catheter body 110. The flexible element duct 206 includes an actuator lumen sized and shaped to receive the flexible element 200 (e.g., the flexible element duct 206 defines the actuator lumen). In one option, the flexible element 200 is slidably coupled with the flexible element duct 206 to facilitate transmission of pushing and pulling forces for deflection of the deflectable distal end portion 102.

In one option, a distal portion 201 of the flexible element 200 extends from the distal end 208 of the flexible element duct 206 toward the distal tip 210 of the catheter body 110. In another option, the flexible element distal portion 201 extends from the distal end 208 of the duct 206 toward a marker band 212. The marker band 212 extends around the catheter liner 202. Optionally, the marker band 212 is coupled to the catheter liner 202 with crimping, adhesives, overmolding or the like. The marker band 212 is fluoroscopic in still another option, facilitating viewing of the deflectable distal end portion 1100 during procedures (e.g., when the catheter body 110 is within vasculature).

As described above, the catheter liner 202, flexible element duct 206, flexible element 200, and the marker band 212 are surrounded by the encapsulant 214. The encapsulant 214 grasps the components and immobilizes them with respect to the catheter body 110. The encapsulant 214 forms the sidewall 215 and at least a portion of the outer surface 217 of the catheter body 110 surrounding the catheter lumen 204. At least the flexible element duct 206 and the flexible element 200 are contained within the encapsulant 214 and outside of the catheter lumen 204.

As shown in FIG. 11, the skirt 220 is disposed around the distal portion 201 of the flexible element 200. The skirt 220 is grasped by the encapsulant 214 to transmit pushing and pulling forces from the flexible element 200 to the deflectable distal end portion 1100 (described above). The skirt 220 is a separate feature from the marker band 212. The skirt 220, as shown in FIG. 11, is proximal to the marker band 212 and separated from the marker band 212 by a space, such as gap 1102. Because the flexible element distal portion 201 is not coupled with the marker band 212 the skirt 220 and the distal portion 201 are spaced a predetermined distance from the marker band 212. The gap 1102, in one option, thereby contains features sandwiched between the skirt 220 and the marker band 212. The features include, but are not limited to, instruments (e.g., for measuring temperature, pressure and the like), electrodes, openings, such as flush openings 1104 and the like. The flush openings 1104 are adapted to discharge fluid, including, but not limited to, saline, contrast media and the like. The flush openings 1104 help to prevent blood clots that form around the catheter body 110, clear out air before procedures and inject contrast media (e.g., for fluoroscopy). Because the gap 1102 is variable, combinations of features are located in the gap 1102, in another option.

Referring to FIGS. 1A, B, C, in operation, the actuator of the handle assembly 150 (e.g., the wheel 104, slide, knob, pull ring and the like) is moved to deflect the deflectable distal end portion 102 from a neutral position (FIG. 1B) to disparate deflected orientations, such as the orientations shown in FIGS. 1A, C. Referring now to FIG. 2, the flexible element 200 is pushed and/or pulled by the actuating mechanisms in the handle assembly 150 to deflect the distal end portion 102. The pushing and pulling forces are transmitted along the flexible element 200 to the flexible element distal portion 201. The distal portion 201, in one option, is coupled to the deflectable distal end portion 102 at the marker band 212 and by encapsulating the skirt 220 within the encapsulant 214. The pushing and pulling forces are transmitted to the catheter liner 202 and the encapsulant 214 by the skirt 220 and the marker band 212. The pushing and pulling forces transmitted by the marker band 212 and the skirt 220 deflect the deflectable distal end portion 102 into a desired orientation (e.g., the orientations shown in FIGS. 1A, C). Optionally, skirts 400A-D, 500A, B, 600, 700 and 800A-D, 900 and 1000 are used in a similar manner during operation of the catheter assembly 100. In another option, multiple skirts are used along the flexible element distal portion 201.

The skirt 220 operates to distribute the pushing and pulling stresses away from the marker band 212 and thereby substantially reduce fracturing of the flexible element distal portion 201 adjacent to the marker band 212, for instance at an annealed region near a weld. Additionally, the skirt 220 and the flexible element 200 have tension and compression strengths equal to or greater than the corresponding tension and compression strengths of the encapsulant 214. Fracture of the flexible element 200 is thereby substantially reduced and the catheter body 110 (FIGS. 1A-C and 2) is adapted to fail before failure of the element 200 and the skirt 220, thereby substantially preventing puncturing of the catheter body 110 with a fractured element.

Optionally, where the flexible element distal portion 201 fractures adjacent to the marker band 212 the skirt 220 substantially immobilizes the distal portion 201 and prevents it from puncturing the catheter body 110. In still another option, a skirt including several features (e.g., knurling, corrugations, flaring or the like) is coupled with the flexible element distal portion 201 to enhance distribution of pushing and pulling forces and further reduce fracturing of the distal portion 201. Additionally, the skirt with multiple features enhances immobilization of a fractured flexible element 200 to further prevent puncturing of the catheter body 110.

Referring now to FIG. 3, in another option, the skirt 220 is used with a flexible element distal portion 201 that is not coupled with the marker band 212. The pushing and pulling forces provided by the flexible element 200 are transmitted to the deflectable distal end portion 102 through the skirt 220 anchored within the encapsulant 214. The pushing and pulling forces transmitted through the skirt 220 operate to deflect the distal end portion 102 into desired orientations, for example, the orientations shown in FIGS. 1A, C. Because the skirt is coupled to the flexible element 200 without welding the element 200 experiences no stresses at an annealed region and the risk of fracturing the flexible element 200 is substantially reduced. As described above, the skirt 220 and the flexible element 200 have tension and compression strengths at least as great as the tension and compression strengths of the encapsulant 214 and thereby substantially reduce fracture of the flexible element 200. Optionally, the catheter body 110 (FIGS. 1A-C and 2) is adapted to fail before failure of the flexible element 200 and the skirt 220, and thereby substantially prevent the puncturing of the catheter body 110 by a fractured element.

Optionally, skirts 400A-D, 500A, B, 600, 700, 800A-D, 900 and 1000 are used in a similar manner to skirt 220 during operation of the catheter assembly 100. In another option, multiple skirts are used along the flexible element distal portion 201. In still another option, a skirt including several features (e.g., knurling, corrugations, flaring or the like) is coupled with the flexible element distal portion 201 to enhance anchoring of the distal portion 201 within the encapsulant 214.

Figure 12:
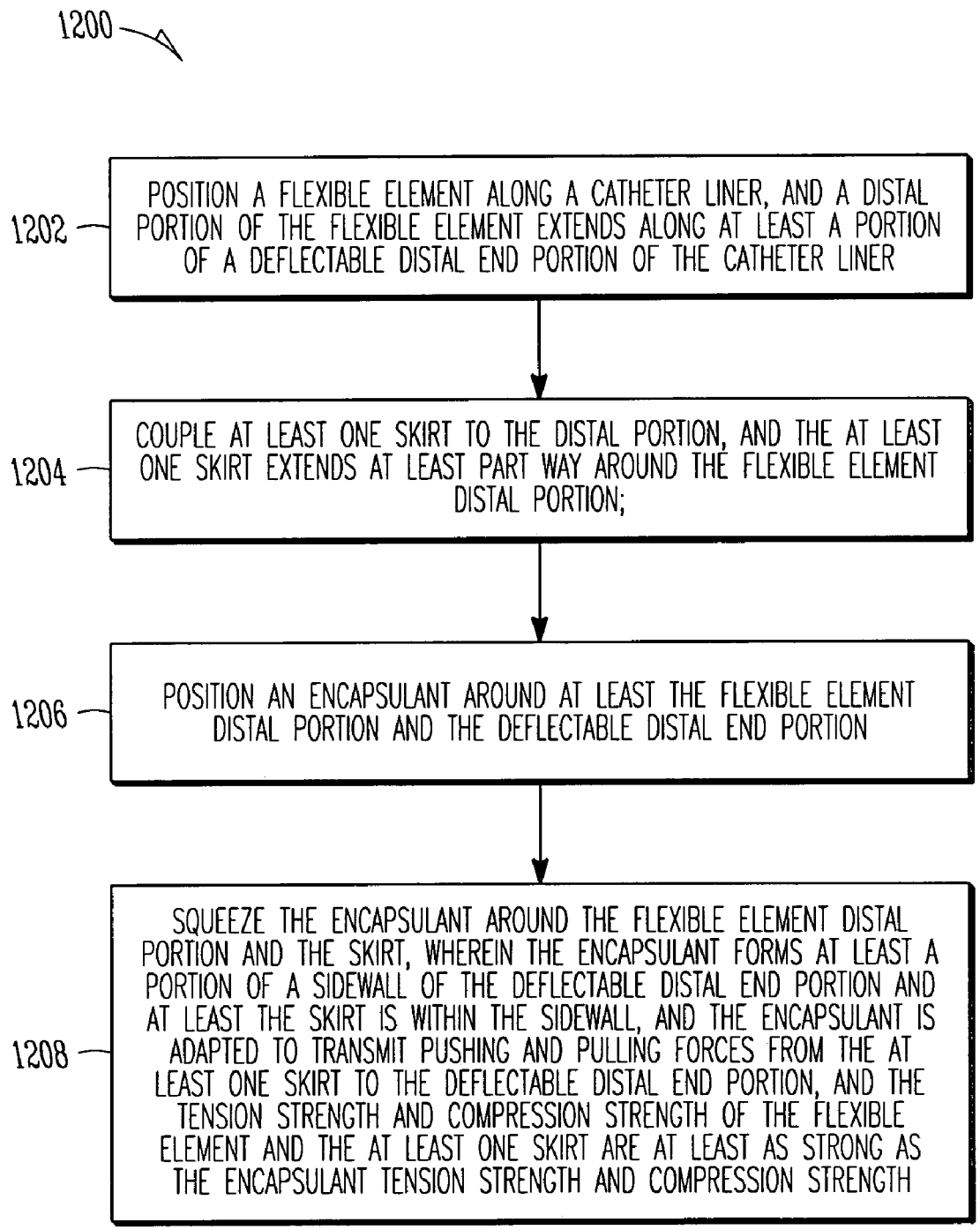
FIG. 12 is a block diagram illustrating one example of a method for making a catheter assembly.

FIG. 12 is a block diagram illustrating one example of a method 1200 for making a catheter body. At 1202 a flexible element is positioned along a catheter liner. A distal portion of the flexible element extends along at least a portion of a deflectable distal end portion of the catheter liner. At 1204 at least one skirt is coupled to the flexible element distal portion, and the at least one skirt extends at least part way around the flexible element distal portion. In one option, the flexible element distal portion proximal to the at least one skirt is free of annealing (e.g., annealing caused by welds). At 1206 an encapsulant (e.g., PEBAX) is positioned around at least the flexible element distal portion and the deflectable distal end portion. At 1208, the encapsulant is squeezed around the flexible element distal portion and the skirt. The encapsulant forms at least a portion of a sidewall of the deflectable distal end portion and at least the skirt is within the sidewall. The encapsulant is adapted to transmit pushing and pulling forces from the at least one skirt to the deflectable distal end portion. Additionally, the tension strength and compression strength of the flexible element and the at least one skirt are at least as strong as the encapsulant tension strength and compression strength. In another option, the encapsulant is adapted to fail before the flexible element and the at least one skirt.

Several options for the method 1200 follow. In one option, the method 1200 includes substantially preventing a puncture of the encapsulant by the flexible element, for instance, by anchoring the skirt within the encapsulant. In another option, a marker band is included in the deflectable distal end portion. The skirt and the flexible element distal portion are positioned proximal to the marker band. The flexible element distal portion and the skirt are spaced proximally from the marker band, optionally, because the flexible element is not coupled to the marker band. Features, such as flushing ports, are formed in the space between the skirt and the marker band, in yet another option. The marker band is coupled to the flexible element distal portion with a weld substantially adjacent to the deflectable distal end portion, in yet another option. Pushing and pulling forces a distributed between the skirt and the marker band to minimizes the forces experienced at the weld. The method 1200 includes, optionally, substantially preventing fracture of the flexible element adjacent to the marker band (e.g., at an annealed or weakened region).

In one option, the method 1200 includes flaring (e.g., by stamping) at least one of the flexible element distal portion and the at least one skirt. In another option, the skirt includes a clamp, and the method 1200 includes deforming the skirt and the skirt grasps the flexible element distal portion. Deforming the skirt includes, optionally, crimping the clamp at a plurality of points along the clamp. In yet another option, the method 1200 includes engaging a projection extending from at least one of the skirt and the flexible element distal portion against the other of the skirt and the distal portion. Engaging the projection includes seating the projection within at least one recess sized and shaped to receive the projection, in still yet another option. The recess is formed in at least one of the skirt and the flexible element distal portion. In a further option, engaging the projection includes using the projection to deform at least one of the flexible element and the skirt. For instance, the projection grasps the flexible element by deforming at least a portion of flexible element. Optionally, the method 1200 includes forming at least one recess (e.g., holes, corrugations, or the like) in the skirt. The at least one recess, in another option, receives the encapsulant and thereby securely anchors the skirt and the flexible element distal portion in the encapsulant. The skirt and the flexible element distal portion are integral and the recesses are formed in the flexible element distal portion, in yet another option.

The above described catheter allows for deflection of a deflectable distal end portion while substantially preventing fracture of a flexible element. Pushing and pulling forces from the flexible element are transmitted through the skirt to the encapsulant and the catheter liner at the deflectable distal end portion of the catheter. The skirt anchored in the encapsulant facilitates deflection of the deflectable distal end portion through transmission of the pushing and pulling forces. In one option, the skirt is integral to the flexible element distal portion. Where the flexible element distal portion is not coupled to a marker band optionally, the skirt and the flexible element are disposed along the catheter body proximal to a marker band used to see the tip of the catheter body during procedures (e.g., with fluoroscopy). Proximally positioning the skirt provides additional space to include features, for instance flush openings and the like, positioned between the skirt and marker band.

The flexible element and the skirt have tension and compression strengths at least as great as the tension and compression strengths of the encapsulant to substantially reduce fracture of the flexible element. Optionally, the catheter body is adapted to fail before failure of the flexible element and the skirt, and puncturing of the catheter body is thereby substantially prevented by a fractured element. In another option, the skirt is coupled to the flexible element distal portion without a weld. Fracturing of the flexible element is thereby substantially reduced because stress is not applied to a weakened annealed region. Additionally, the skirt is localized around the flexible element without extending remotely around the deflectable distal end portion. The skirt thus provides improved strength and durability against failure through shearing. Moreover, because the skirt is localized substantially adjacent to the flexible element pushing and pulling forces are not distributed around the catheter body. The deflectable distal end portion thus experiences an improved deflection response with the concentrated pushing and pulling of the flexible element.

In another option, the skirt cooperates with the marker band coupled to the flexible element distal portion. The marker band is coupled to the flexible element distally relative to the skirt. The skirt acts as a supplementary anchor and distributes pushing and pulling forces between the marker band and itself. Fracturing of the flexible element adjacent to the marker band (e.g., the annealed region near a weld) is substantially reduced because the pushing and pulling forces are distributed between the skirt and the marker band. Additionally, where the flexible element distal portion does fracture adjacent the marker band, the skirt embedded in the encapsulant acts to substantially immobilize the fractured flexible element and substantially prevent puncturing of the catheter body. Moreover, the skirt facilitates continued use of the catheter with a fractured flexible element because the skirt continues to function as an anchor and transmits pushing and pulling forces to the deflectable distal end portion.

Additionally, the encapsulant is squeezed around the catheter liner to easily form an outer surface and sidewall of the catheter body and grasp the skirt. In one option, the skirt is in the sidewall and thereby provides a larger moment to the deflectable distal end portion because it is positioned remotely from the center of the catheter body. As described above, the encapsulant flows around the skirt and, when hardened, transmits tension and compression forces to the deflectable distal end portion while also acting as the outer surface of the catheter body. Complex manufacturing procedures including drilling and/or forming a pocket for an anchor and injecting an adhesive over the anchor are thereby avoided. Further, the skirt is retained along the catheter body and the distal end therefore does not house the skirt and/or the flexible element in a hard tip. In one option, the distal end of the catheter body thereby has a soft atraumatic tip.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the invention should, therefore, be determined with reference to the appended claims, along with the full scope of equivalents to which such claims are entitled.

What is claimed is:

1. A deflectable catheter comprising:
   a catheter body including a deflectable distal end portion;
   a flexible element including a flexible element distal portion extending along at least a portion of the deflectable distal end portion;
   at least one skirt extending at least part way around the flexible element distal portion and secured to the flexible element distal portion at a deformed portion of the skirt, the at least one skirt including a flared projection at one or both of a skirt proximal end or a skirt distal end; and the flexible distal end portion is at least partially received within the flared projection;
   an encapsulant coupled between the at least one skirt and the deflectable distal end portion, wherein the encapsulant is adapted to transmit pushing and pulling forces from the at least one skirt to the deflectable distal end portion, the encapsulant is received within the flared projection, and the encapsulant forms at least a portion of an outer surface of the deflectable distal end portion; and
   wherein the tension strength and compression strength of the flexible element and the at least one skirt are at least as strong as the encapsulant tension strength and compression strength.

2. The deflectable catheter of claim 1, wherein the at least one skirt includes at least one recess dimensioned and configured to receive the encapsulant.

3. The deflectable catheter of claim 1, wherein the at least one skirt is integral to the flexible element distal portion.

4. The deflectable catheter of claim 1, wherein the flared projection extends less than about half way around the deflectable distal end portion.

5. The deflectable catheter of claim 1, wherein the at least one skirt includes a clamp substantially surrounding the flexible element distal portion.

6. The deflectable catheter of claim 5, wherein the clamp is deformed and grasps the flexible element distal portion.

7. The deflectable catheter of claim 6, wherein the clamp is crimped at a plurality of points along the clamp.

8. The deflectable catheter of claim 1, wherein at least one of the skirt and the flexible element distal portion include at least one projection.

9. The deflectable catheter of claim 8, wherein at least one of the skirt and the flexible element distal portion include at least one recess sized and shaped to receive the at least one projection.

10. The deflectable catheter of claim 8, wherein the at least one projection extends from the at least one skirt and engages against the flexible element distal portion substantially immobilizing the at least one skirt relative to the flexible element.

11. The deflectable catheter of claim 1, wherein the at least one skirt and at least the flexible element proximal to the at least one skirt are free of welding.

12. A deflectable catheter assembly comprising:
    a catheter body extending from a proximal end to a deflectable distal end portion, wherein the catheter body includes a sidewall surrounding a catheter lumen, and an actuator lumen within the side wall extends from the proximal end to an intermediate portion proximal to the deflectable distal end portion;

a flexible element extending through the actuator lumen, wherein a flexible element distal portion extends from the intermediate portion along at least a portion of the deflectable distal end portion;

at least one skirt secured to the flexible element distal portion and within the sidewall, wherein the at least one skirt extends at least part way around the flexible element distal portion, the skirt includes a proximal projection with a proximal tapered portion tapering toward a skirt distal end, and the skirt includes a distal projection with a distal tapered portion tapering toward a skirt proximal end;

an encapsulant coupled between the at least one skirt and the deflectable distal end portion, wherein the encapsulant is adapted to transmit tension and compression from the at least one skirt to the deflectable distal end portion, and the encapsulant forms at least a portion of the side wall of the deflectable distal end portion; and wherein the catheter body is adapted to fail before failure of the flexible element and the skirt.

13. The deflectable catheter assembly of claim 12, wherein at least one weld couples the flexible element distal portion to the deflectable distal end portion and the at least one weld is distal to the at least one skirt.

14. The deflectable catheter assembly of claim 13, wherein the deflectable distal end portion includes a marker band and the weld couples the flexible element distal portion to the marker band.

15. The deflectable catheter assembly of claim 13, wherein the deflectable distal end portion includes a marker band and the flexible element distal portion and the at least one skirt are proximal to the marker band.

16. The deflectable catheter assembly of claim 15, wherein at least one flush opening is provided between the marker band and the flexible element distal portion and the at least one skirt.

17. The deflectable catheter assembly of claim 12, wherein at least one of the proximal projection and the distal projection includes a flared projection extending annularly away from the flexible element, and the flared projection includes a conical geometry.

18. The deflectable catheter assembly of claim 17, wherein the encapsulant fills at least a portion of the conical geometry.

19. The deflectable catheter assembly of claim 12, wherein the flexible element has substantially the same strength in tension and compression along an entire flexible element length, and the at least one skirt has substantially the same strength in tension and compression along an entire anchor length.

20. A deflectable catheter assembly comprising:
a catheter body extending from a catheter proximal end to a catheter deflectable distal end portion, the catheter body including:
  a catheter side wall, the catheter sidewall including an encapsulant forming a smooth catheter outer surface around the catheter deflectable distal end portion,
  a catheter delivery lumen surrounded by the encapsulant, and
  a flexible element duct disposed within the catheter sidewall, the flexible element duct extends from near the catheter proximal end toward the catheter deflectable distal end portion;
a flexible element extending through the flexible element duct toward the catheter deflectable distal end portion, the flexible element is slidably disposed within the flexible element duct; and
at least one anchor fixedly engaged along the flexible element near the catheter deflectable distal end portion, the at least one anchor includes a deformed inner surface engaged against the flexible element, the at least one anchor including an exposed portion distinct from the deformed inner surface, the exposed portion including:
  a deformed outer surface at an intermediate portion of the at least one anchor, and the deformed outer surface is secured on the flexible element,
  a flared projection extending radially away from the flexible element, the flared projection is at one of an anchor proximal end or an anchor distal end, and a tapered portion of the flared projection of the anchor tapers toward the intermediate portion of the anchor,
wherein the at least one anchor is fully surrounded by the encapsulant around the deformed outer surface and the flared projection, and the encapsulant fills a space between the flared projection and the flexible element, and pushing and pulling forces are transmitted entirely through the encapsulant to the catheter deflectable distal end portion.

21. The deflectable catheter assembly of claim 20, wherein the flared projection extends annularly away from the flexible element, and the flared projection includes a conical geometry.

22. The deflectable catheter assembly of claim 21, wherein the encapsulant fills at least a portion of the conical geometry.

23. The deflectable catheter assembly of claim 20, wherein the at least one anchor includes a first flared projection at an anchor proximal end and a second flared projection at an anchor distal end.

24. The deflectable catheter assembly of claim 23, wherein the first flared projection extends proximally toward the catheter proximal end, and the second flared projection extends distally toward a catheter distal end.

25. The deflectable catheter assembly of claim 20, wherein the flexible element has substantially the same strength in tension and compression along an entire flexible element length.

26. The deflectable catheter assembly of claim 20, wherein the at least one anchor has substantially the same strength in tension and compression along an entire anchor length.

27. The deflectable catheter assembly of claim 20, wherein the at least one anchor and the flexible element are free of welding.

28. The deflectable catheter assembly of claim 20, wherein the deformed inner surface includes a clamp substantially surrounding the flexible element, and the clamp grasps the flexible element and immobilizes the at least one anchor relative to the flexible element.

* * * * *

UNITED STATES PATENT AND TRADEMARK OFFICE
CERTIFICATE OF CORRECTION

PATENT NO. : 7,553,305 B2  
APPLICATION NO. : 11/149079  
DATED : June 30, 2009  
INVENTOR(S) : Brian Honebrink et al.

It is certified that error appears in the above-identified patent and that said Letters Patent is hereby corrected as shown below:

On the title page, item (57), under "Abstract", in column 2, lines 1-2, after "element" delete "includes a flexible element".

Signed and Sealed this

Thirteenth Day of October, 2009

David J. Kappos  
*Director of the United States Patent and Trademark Office*